(12) United States Patent
Kobayashi et al.

(10) Patent No.: US 12,263,045 B2
(45) Date of Patent: Apr. 1, 2025

(54) SURGICAL ROBOT AND CONTROL METHOD OF SURGICAL ROBOT

(71) Applicant: KAWASAKI JUKOGYO KABUSHIKI KAISHA, Kobe (JP)

(72) Inventors: Ayataka Kobayashi, Kobe (JP); Tetsuo Ichii, Kobe (JP); Hirofumi Yamamori, Kobe (JP); Hideo Kawabata, Kobe (JP); Hiroaki Kitatsuji, Kobe (JP)

(73) Assignee: KAWASAKI JUKOGYO KABUSHIKI KAISHA, Kobe (JP)

( * ) Notice: Subject to any disclaimer, the term of this patent is extended or adjusted under 35 U.S.C. 154(b) by 382 days.

(21) Appl. No.: 17/837,076

(22) Filed: Jun. 10, 2022

(65) Prior Publication Data

US 2022/0395350 A1   Dec. 15, 2022

(30) Foreign Application Priority Data

Jun. 15, 2021   (JP) .................. 2021-099667

(51) Int. Cl.
| | |
|---|---|
| A61B 90/00 | (2016.01) |
| A61B 34/00 | (2016.01) |
| A61B 34/10 | (2016.01) |
| A61B 34/20 | (2016.01) |
| A61B 34/30 | (2016.01) |
| A61B 34/35 | (2016.01) |
| A61B 50/13 | (2016.01) |

(52) U.S. Cl.
CPC .............. *A61B 90/37* (2016.02); *A61B 34/10* (2016.02); *A61B 34/35* (2016.02); *A61B 34/74* (2016.02); *A61B 50/13* (2016.02); *A61B 2034/107* (2016.02); *A61B 2034/2055* (2016.02); *A61B 2034/2074* (2016.02); *A61B 2034/254* (2016.02); *A61B 2034/301* (2016.02); *A61B 2090/365* (2016.02)

(58) Field of Classification Search
CPC ......... A61B 90/37; A61B 34/10; A61B 34/35; A61B 34/74; A61B 50/13; A61B 2034/107; A61B 2034/2055; A61B 2034/2074; A61B 2034/254; A61B 2034/301; A61B 2034/365
See application file for complete search history.

(56) References Cited

U.S. PATENT DOCUMENTS

| | | | |
|---|---|---|---|
| 2008/0004603 A1* | 1/2008 | Larkin | A61B 34/25 606/1 |
| 2017/0095298 A1* | 4/2017 | Vakharia | A61B 18/1445 |
| 2020/0214774 A1* | 7/2020 | Yoshida | A61B 50/13 |
| 2021/0068907 A1 | 3/2021 | Fuerst et al. | |

(Continued)

FOREIGN PATENT DOCUMENTS

| | | |
|---|---|---|
| JP | 2019-528878 A | 10/2019 |
| WO | 2014/122750 A1 | 8/2014 |
| WO | 2018/052796 A1 | 3/2018 |

*Primary Examiner* — Ryan J. Severson
*Assistant Examiner* — Cherie M Poland
(74) *Attorney, Agent, or Firm* — METROLEX IP LAW GROUP, PLLC; Robert L. Scott, Esq.

(57) ABSTRACT

A surgical robot includes a controller configured or programmed to control a display to superimpose guide information indicating a moving direction of a medical cart based on a steering angle of a steering device on an image captured by an imaging device and display the guide information.

20 Claims, 14 Drawing Sheets

(56) References Cited

U.S. PATENT DOCUMENTS

| | | | |
|---|---|---|---|
| 2022/0233255 A1* | 7/2022 | Kawabata | G16H 40/67 |
| 2024/0050175 A1* | 2/2024 | Kishida | A61B 34/30 |
| 2024/0217115 A1* | 7/2024 | Mizohata | B25J 13/06 |

* cited by examiner

SURGICAL ROBOT AND CONTROL METHOD OF SURGICAL ROBOT

CROSS-REFERENCE TO RELATED APPLICATION

The present application claims priority to JP2021-099667, which is incorporated herein by reference.

BACKGROUND OF THE INVENTION

Field of the Invention

The present disclosure relates to a surgical robot and a control method of a surgical robot.

Description of the Background Art

Conventionally, a surgical robot including a medical cart to move a robot main body including arms is known. For example, a surgical manipulator assembly including an arm and a base supporting the base end of the arm is disclosed in Japanese Translation of PCT International Application Publication No. 2019-528878. In Japanese Translation of PCT International Application Publication No. 2019-528878, a surgical instrument is attached to the tip end of the arm. The arm is remotely controlled such that surgery is performed on a patient by the surgical instrument attached to the tip end of the arm.

The surgical manipulator assembly disclosed in Japanese Translation of PCT International Application Publication No. 2019-528878 includes a setup assembly that supports the base above the floor surface. The setup assembly includes a cart that moves with respect to the floor surface and a setup arm extending horizontally from the cart. The base that supports the base end of the arm is arranged at the tip end of the setup arm. An operator manually operates at least one of the cart or the setup assembly to position the base with respect to the patient.

In the surgical manipulator assembly disclosed in Japanese Translation of PCT International Application Publication No. 2019-528878, an indicator light is arranged to position the base. The indicator light projects light toward the floor surface of an operating room in which the patient is located. A direction in which the light is projected indicates a direction in which at least one of the base or the cart is moved, and the operator moves at least one of the base or the cart in the direction of the projected light. Thus, the base is moved to an optimum position.

However, in the surgical manipulator assembly disclosed in Japanese Translation of PCT International Application Publication No. 2019-528878, the direction of the light emitted toward the floor surface in the operating room only indicates the moving direction of at least one of the base or the cart on the floor surface. Thus, the arm cannot conceivably be accurately positioned with respect to the patient after movement of the arm.

SUMMARY OF THE INVENTION

The present disclosure is intended to solve the above problem. The present disclosure aims to provide a surgical robot and a control method of a surgical robot each capable of accurately positioning an arm with respect to a patient.

In order to attain the aforementioned object, a surgical robot according to a first aspect of the present disclosure includes a robot main body including a manipulator arm to which a surgical instrument is attached, a medical cart including a steering device to receive an operator's steering operation, the medical cart moving the robot main body based on the received operator's steering operation, an imaging device on the robot main body, a display to display an image captured by the imaging device, and a controller configured or programmed to control the display to superimpose guide information indicating a moving direction of the medical cart based on a steering angle of the steering device on the image captured by the imaging device and display the guide information.

In the surgical robot according to the first aspect of the present disclosure, as described above, the controller is configured or programmed to control the display to superimpose the guide information indicating the moving direction of the medical cart based on the steering angle of the steering device on the image captured by the imaging device and display the guide information. Accordingly, the image captured by the imaging device is displayed on the display together with the guide information, and thus the operator easily understands the relative positional relationship between the moving direction of the medical cart and a patient. Therefore, the operator can move the medical cart to an appropriate position with respect to the patient according to the guide information. Consequently, the manipulator arm can be accurately positioned with respect to the patient.

A control method of a surgical robot according to a second aspect of the present disclosure includes capturing an image by an imaging device, displaying an image of a patient captured by the imaging device on a display, receiving a steering operation on a steering device of a medical cart that moves a robot main body including a manipulator arm to which a surgical instrument is attached, and superimposing guide information indicating a moving direction of the medical cart based on a steering angle of the steering device on the image captured by the imaging device and displaying the guide information on the display.

As described above, the control method of a surgical robot according to the second aspect of the present disclosure includes the superimposing of the guide information indicating the moving direction of the medical cart based on the steering angle of the steering device on the image captured by the imaging device and the displaying of the guide information on the display. Accordingly, the image captured by the imaging device is displayed on the display together with the guide information, and thus an operator easily understands the relative positional relationship between the moving direction of the medical cart and the patient. Therefore, the operator can move the medical cart to an appropriate position with respect to the patient according to the guide information. Consequently, it is possible to provide the control method of a surgical robot capable of accurately positioning the manipulator arm with respect to the patient.

According to the present disclosure, as described above, the manipulator arm can be accurately positioned with respect to the patient.

The foregoing and other objects, features, aspects and advantages of the present disclosure will become more apparent from the following detailed description of the present disclosure when taken in conjunction with the accompanying drawings.

DESCRIPTION OF THE PREFERRED EMBODIMENTS

Figure 1:
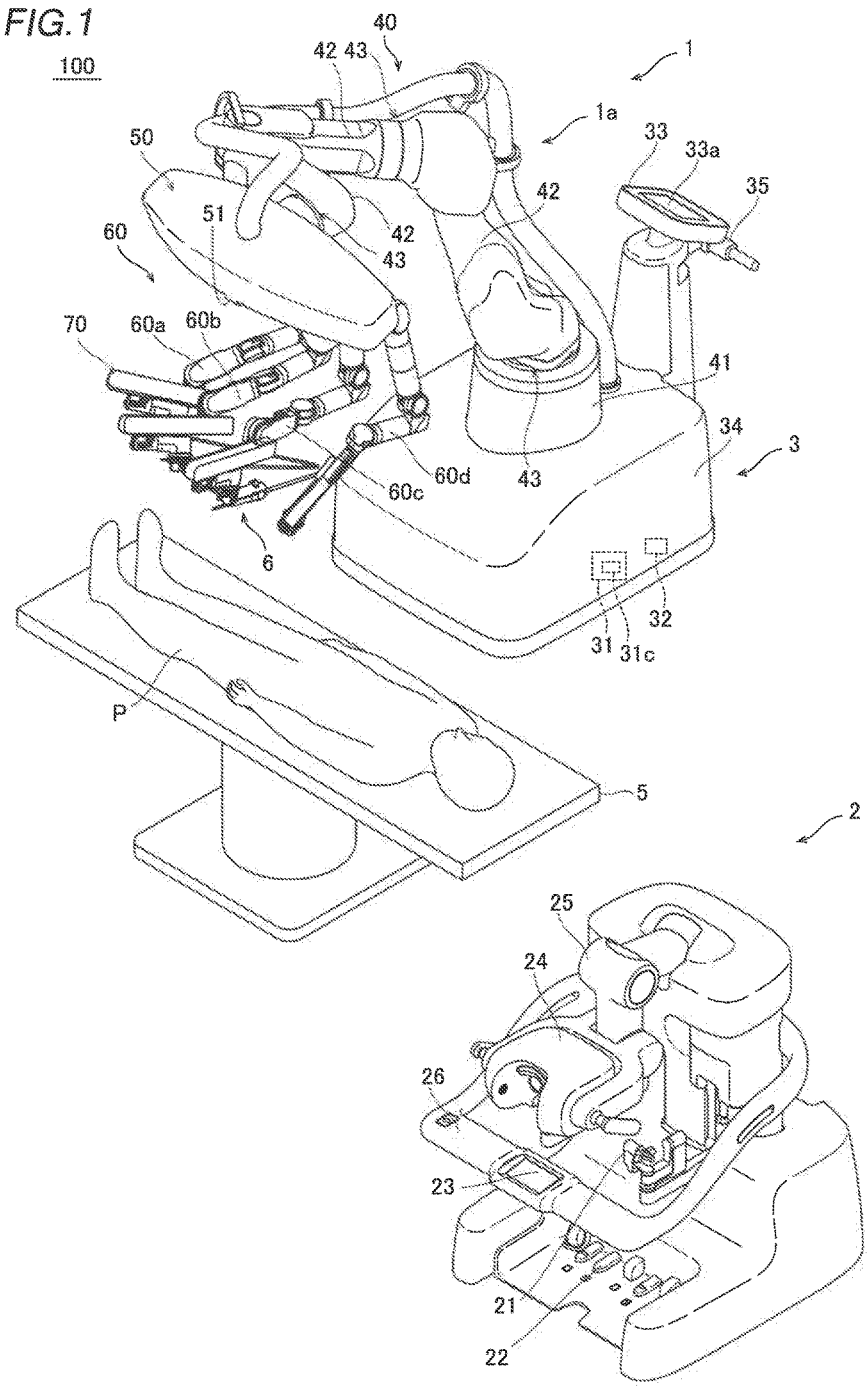
FIG. 1 is a diagram showing the configuration of a surgical system according to an embodiment of the present disclosure.

An embodiment of the present disclosure is hereinafter described with reference to the drawings.

The configuration of a surgical system 100 according to this embodiment is now described with reference to FIGS. 1 to 24. The surgical system 100 includes a medical manipulator 1 that is a patient P-side apparatus and a remote control apparatus 2 that is an operator-side apparatus to operate the medical manipulator 1. The medical manipulator 1 includes a medical cart 3 and is movable. The remote control apparatus 2 is spaced apart from the medical manipulator 1, and the medical manipulator 1 is remotely operated by the remote control apparatus 2. A surgeon inputs a command to the remote control apparatus 2 to cause the medical manipulator 1 to perform a desired operation. The remote control apparatus 2 transmits the input command to the medical manipulator 1. The medical manipulator 1 operates based on the received command. The medical manipulator 1 is arranged in an operating room that is a sterilized sterile field. The medical manipulator 1 is an example of a surgical robot.

The remote control apparatus 2 is arranged inside or outside the operating room, for example. The remote control apparatus 2 includes operation manipulator arms 21, operation pedals 22, a touch panel 23, a monitor 24, a support arm 25, and a support bar 26. The operation manipulator arms 21 define operation handles for the surgeon to input commands. The monitor 24 is a scope-type display that displays an image captured by an endoscope 6. The support arm 25 supports the monitor 24 so as to align the height of the monitor 24 with the height of the surgeon's face. The touch panel 23 is arranged on the support bar 26. The surgeon's head is detected by a sensor provided in the vicinity of the monitor 24 such that the medical manipulator 1 can be operated by the remote control apparatus 2. The surgeon operates the operation manipulator arms 21 and the operation pedals 22 while visually recognizing an affected area on the monitor 24. Thus, a command is input to the remote control apparatus 2. The command input to the remote control apparatus 2 is transmitted to the medical manipulator 1.

The medical cart 3 includes a controller 31 that controls the operation of the medical manipulator 1 and a storage 32 that stores programs or the like to control the operation of the medical manipulator 1. The controller 31 of the medical cart 3 controls the operation of the medical manipulator 1 based on the command input to the remote control apparatus 2.

The medical cart 3 includes an input 33. The input 33 receives operations to move a positioner 40, an arm base 50, and a plurality of manipulator arms 60 or change their postures mainly in order to prepare for surgery before the surgery. A robot main body 1a is formed by the positioner 40, the arm base 50, and the plurality of manipulator arms 60.

Figure 2:
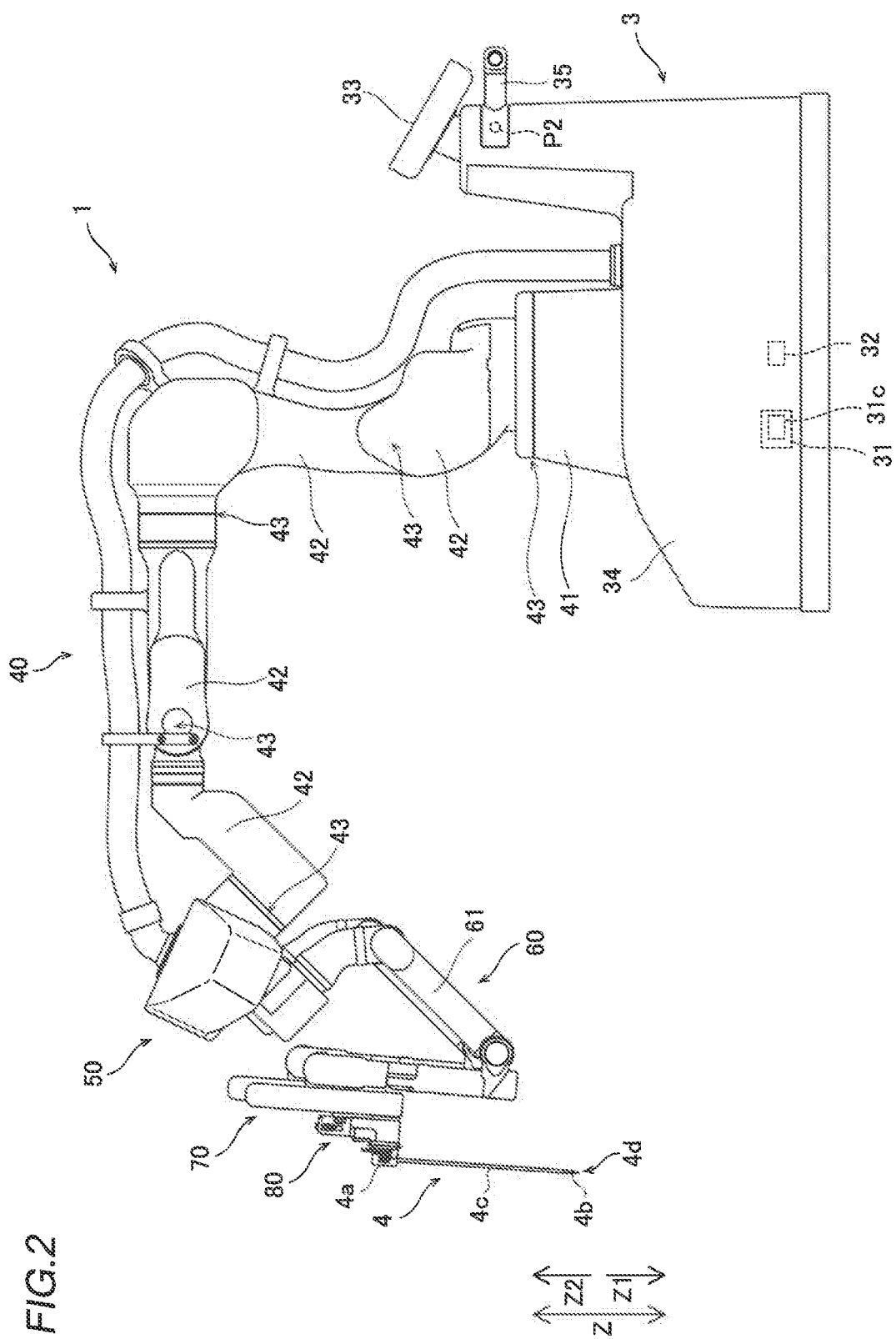
FIG. 2 is a diagram showing the configuration of a medical manipulator according to the embodiment of the present disclosure.

As shown in FIGS. 1 and 2, the medical manipulator 1 is arranged in the operating room. The medical manipulator 1 includes the medical cart 3, the positioner 40, the arm base 50, and the plurality of manipulator arms 60. The arm base 50 is attached to the tip end of the positioner 40. The arm base 50 has a relatively long rod shape. The bases of the plurality of manipulator arms 60 are attached to the arm base 50. Each of the plurality of manipulator arms 60 is able to take a folded and stored posture. The arm base 50 and the plurality of manipulator arms 60 are covered with sterile drapes and used.

In this embodiment, the arm base 50 includes an imaging device 51. The imaging device 51 images a patient P placed on a surgical table 5. The imaging device 51 is provided to align the arm base 50 and the manipulator arms 60 with the patient P who is placed on the surgical table 5 and has trocars T inserted into their body surface S.

The positioner 40 includes a 7-axis articulated robot, for example. The positioner 40 is arranged on a casing 34 of the medical cart 3. The positioner 40 moves the arm base 50. Specifically, the positioner 40 moves the position of the arm base 50 three-dimensionally.

The positioner 40 includes a base 41 and a plurality of links 42 coupled to the base 41. The plurality of links 42 are coupled to each other by joints 43.

As shown in FIG. 2, a surgical instrument 4 is attached to the tip end of each of the plurality of manipulator arms 60.

Figure 7:
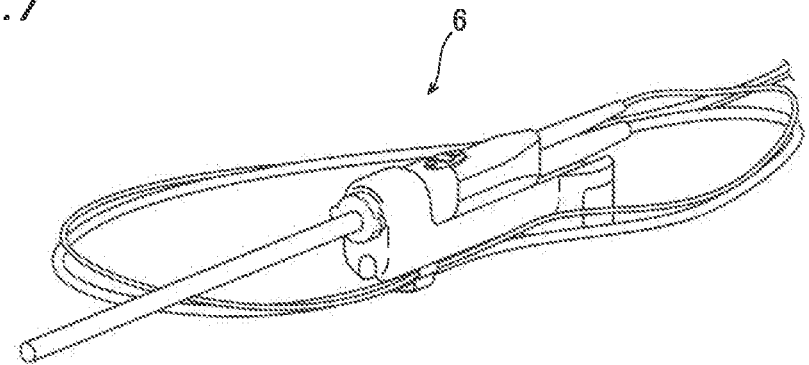
FIG. 7 is a diagram showing an endoscope.

The surgical instrument 4 includes a replaceable instrument or the endoscope 6 shown in FIG. 7, for example.

As shown in FIG. 2, the instrument as the surgical instrument 4 includes a driven unit 4a driven by servomotors M2 provided in a holder 71 of each of the manipulator arms 60. An end effector 4b is provided at the tip end of the instrument. The end effector 4b includes a pair of forceps, a pair of scissors, a grasper, a needle holder, a microdissector, a stable applier, a tacker, a suction cleaning tool, a snare wire, a clip applier, etc. as instruments having joints. The end effector 4b includes a cutting blade, a cautery probe, a washer, a catheter, a suction orifice, etc. as instruments having no joint. The surgical instrument 4 includes a shaft 4c that connects the driven unit 4a to the end effector 4b. The driven unit 4a, the shaft 4c, and the end effector 4b are arranged along a Z direction.

Figure 3:
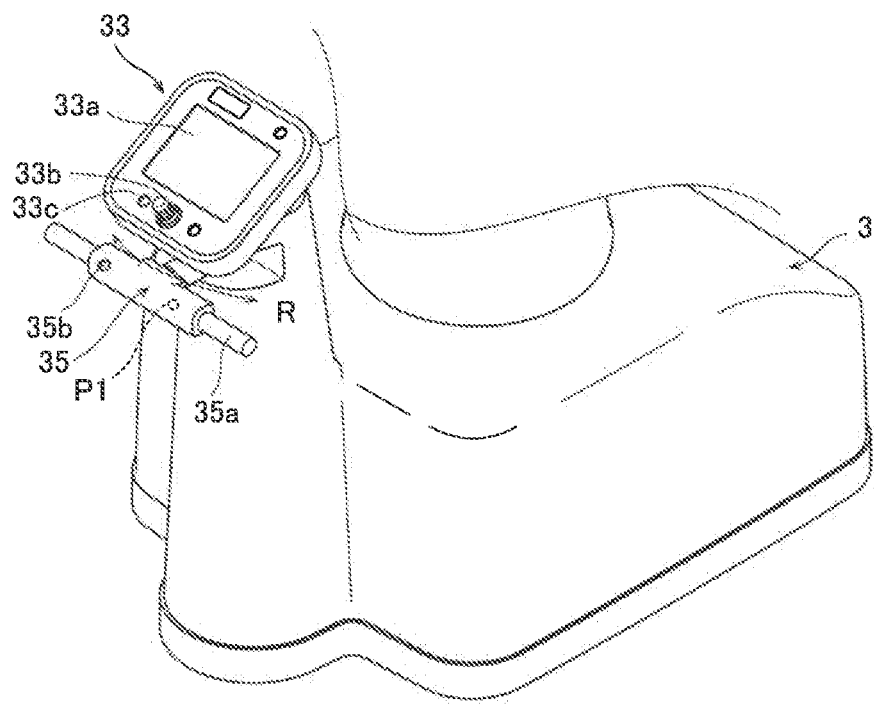
FIG. 3 is a perspective view showing the configuration of a medical cart according to the embodiment of the present disclosure.
Figure 4:
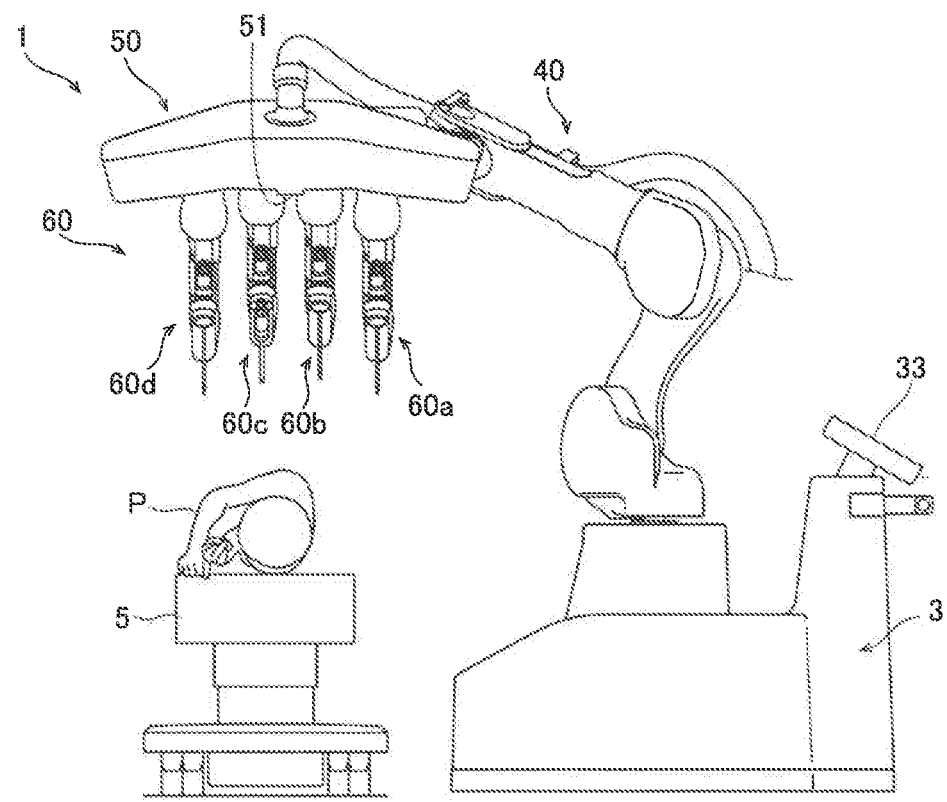
FIG. 4 is a diagram showing a roll-in posture.
Figure 5:
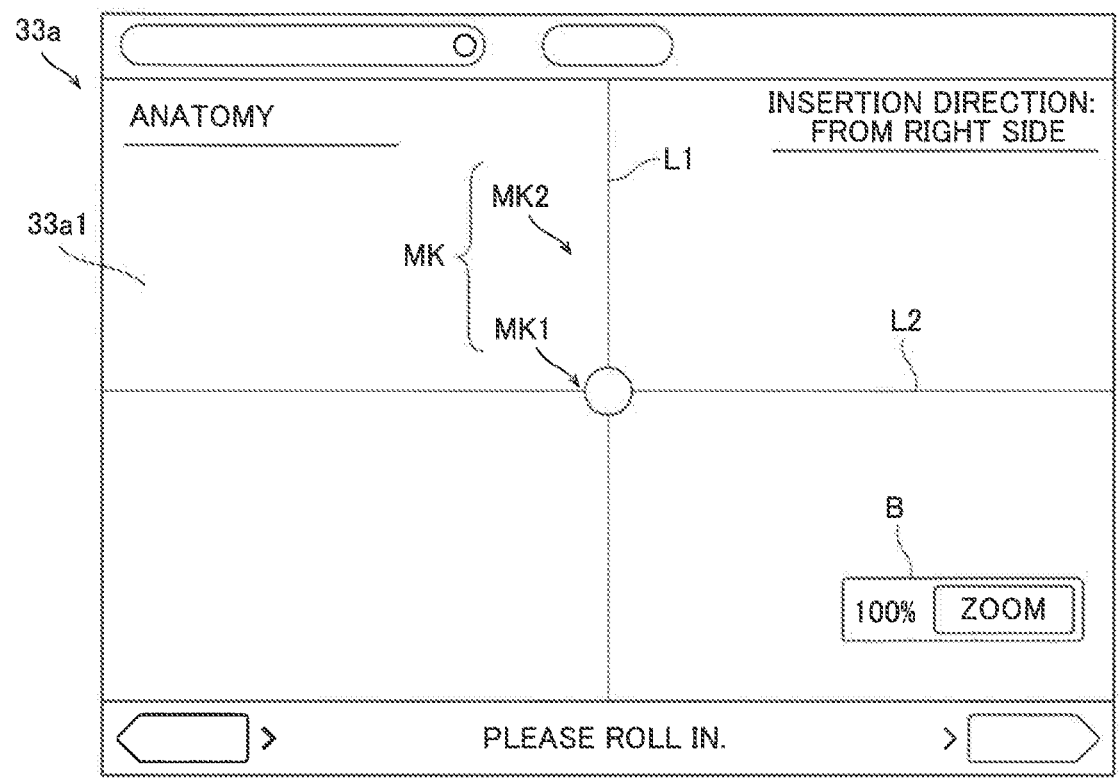
FIG. 5 is a diagram showing marks displayed on a display.
Figure 6:
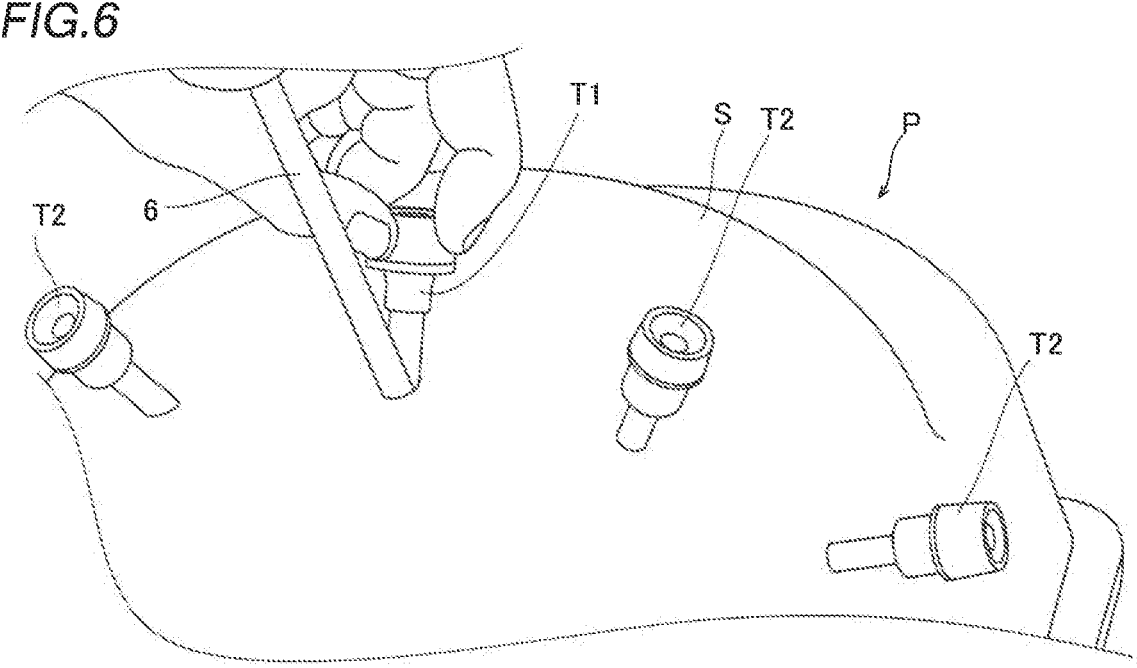
FIG. 6 is a diagram showing trocars inserted into the body surface of a patient.

In this embodiment, as shown in FIGS. 3 and 4, the medical cart 3 includes a display 33a to display an image captured by the imaging device 51 in real time. The display 33a is arranged on the input 33 of the medical cart 3. The display 33a displays the patient P imaged by the imaging device 51 in real time. As shown in FIG. 5, on the display 33a, the image of the patient P captured by the imaging device 51 and marks MK for aligning the arm base 50 with the patient P are superimposed and displayed. Specifically, on the display 33a, an image of the trocars T shown in FIG. 6 for inserting the endoscope 6 from the body surface S of the patient P captured the imaging device 51 and the marks MK for aligning the arm base 50 with the trocars T are superimposed and displayed. The marks MK displayed on the display 33a are aligned, on the display 33a, with the trocars T displayed on the display 33a such that the manipulator arms 60 are aligned with a surgical location in the patient P placed on the surgical table 5.

The image of the patient P and the trocars T displayed on the display 33a is an image actually captured by the imaging device 51, and the marks MK are graphical user interface (GUI) images generated by the controller 31 and are stored in the storage 32. The controller 31 is equipped with an image processing circuit 31c shown in FIGS. 1 and 2 that displays an image obtained from the imaging device 51 on the display 33a. The image processing circuit 31c using a field programmable gate array (FPGA) mounted on the controller 31 synthesizes and displays the image of the patient P and the trocars T actually captured by the imaging device 51 and stored in the storage 32 and both the marks MK of the GUI images and a guideline GL described below on the display 33a in real time with a delay that people do not recognize. The image processing circuit 31c may include an application specific integrated circuit (ASIC) or a system on a chip (SoC), for example, other than the field programmable gate array (FPGA). The image processing circuit 31c is an example of a controller.

Specifically, the trocars T includes a first trocar T1 into which the endoscope 6 is inserted and second trocars T2 into which the surgical instruments 4 other than the endoscope 6 are inserted. The marks MK displayed on the display 33a include a first mark MK1 aligned with the first trocar T1 on the display 33a and a second mark MK2 aligned with the second trocars T2 on the display 33a. More specifically, the first mark MK1 is displayed on a substantially central portion of the display 33a and has a substantially circular shape. The second mark MK2 has a cross shape centered on the substantially circular first mark MK1. The second mark MK2 has a cross shape that intersects at the center of the substantially circular first mark MK1. The first mark MK1 is an example of a mark. The first trocar T1 is an example of a trocar.

The size of the substantially circular first mark MK1 is larger than the size of the first trocar T1 displayed on the display 33a. Specifically, the diameter of the substantially circular first mark MK1 is larger than the diameter of the first trocar T1 having a substantially circular cross-section.

A plurality of second trocars T2 are provided on the body surface S of the patient P. The plurality of second trocars T2 are arranged on a substantially straight line. The trocars T are arranged in the order of the second trocar T2, the first trocar T1, the second trocar T2, and the second trocar T2 so as to correspond to the plurality of manipulator arms 60. In this embodiment, the number of manipulator arms 60 is four.

The display 33a has a substantially rectangular shape. For example, the display 33a has a horizontally long rectangular shape as viewed from an operator. The cross-shaped second mark MK2 includes a substantially linear first line L1 provided along the longitudinal direction of the substantially rectangular display 33a, and a substantially linear second line L2 provided along the transverse direction of the substantially rectangular display 33a. The medical manipulator 1 is configured such that the plurality of second trocars T2 are aligned along the first line L1 or the second line L2 on the display 33a.

The display of the first line L1 and the second line L2 on the display 33a is fixed on the display 33a. The display 33a is fixed to the medical cart 3. Thus, a direction along the first line L1 corresponds to the moving direction of the medical cart 3. The moving direction of the medical cart 3 refers to a forward-rearward direction. The image of the patient P displayed on the display 33a changes with movement of the arm base 50 or movement of the medical cart 3.

A magnification change button B is displayed to enlarge or reduce an image of the first mark MK1 together with the image of the patient P displayed on the display 33a. The magnification change button B is displayed on a touch panel. When the magnification change button B is pressed, the magnification percentage of an image is changed in a loop of 100%, 200%, 400%, 100%, and 200%. When the magnification percentage of the image is 100%, the end of the surgical table 5 and a nearby assistant and nurse are displayed on the display 33a.

The first trocar T1 displayed on the display 33a and the first mark MK1 are aligned with each other on the display 33a, and the second trocars T2 displayed on the display 33a and the second mark MK2 are aligned with each other on the display 33a such that the manipulator arms 60 are aligned with the surgical location in the patient P placed on the surgical table 5. The details of alignment of the manipulator arms 60 with the surgical location in the patient P are described below. The alignment of the manipulator arms 60 with the surgical location in the patient P is called roll-in.

As shown in FIG. 3, a joystick 33b for operating movement of the positioner 40 is provided in the vicinity of the display 33a of the medical cart 3. The positioner 40 can be operated three-dimensionally by selecting an operation mode displayed on the display 33a and operating the joystick 33b. At the time of roll-in, the joystick 33b is operated such that the positioner 40 is moved so as to move the arm base 50 on a two-dimensional plane. On the display 33a, the trocars T displayed on the display 33a and the marks MK are aligned with each other. Specifically, the joystick 33b is provided at a substantially central portion of the display 33a in the transverse direction and below the display 33a on the input 33.

An enable switch 33c for allowing or disallowing movement of the positioner 40 is provided in the vicinity of the joystick 33b of the medical cart 3. The joystick 33b is operated while the enable switch 33c is being pressed to allow the positioner 40 to move such that the positioner 40 is moved. Specifically, the enable switch 33c is provided below the display 33a and adjacent to the joystick 33b on the input 33.

In this embodiment, the medical cart 3 includes an operation handle 35 to receive an operator's steering operation. The medical cart 3 moves the robot main body 1a based on the received operator's steering operation. The operation handle 35 is an example of a steering device.

The operation handle 35 is arranged in the vicinity of the display 33a of the medical cart 3. The operation handle 35 includes a throttle 35a that is gripped and rotated by the operator such as a nurse or a technician to operate movement of the medical cart 3. Specifically, the operation handle 35 is arranged below the input 33. As shown in FIG. 3, the throttle 35a is arranged on one side of the operation handle 35. The throttle 35a is rotated from the front side to the rear side such that the medical cart 3 moves forward. The throttle 35a is rotated from the rear side to the front side such that the medical cart 3 moves rearward. The speed of the medical cart 3 is changed according to the amount of rotation of the throttle 35a. The operation handle 35 is rotatable to the left and right shown as an R direction, and the medical cart 3 is turned with rotation of the operation handle 35.

An enable switch 35b for allowing or disallowing movement of the medical cart 3 is provided on the operation handle 35 of the medical cart 3. The throttle 35a of the operation handle 35 is operated while the enable switch 35b is being pressed to allow the medical cart 3 to move such that the medical cart 3 is moved.

While the trocars T displayed on the display 33a and the marks MK are aligned with each other on the display 33a, the positioner 40 is controlled such that the arm base 50 is moved in order for the imaging device 51 to image a region vertically therebelow. This control is performed by the controller 31 that controls the operation of the medical manipulator 1.

The configuration of the manipulator arms 60 is now described in detail.

Figure 8:
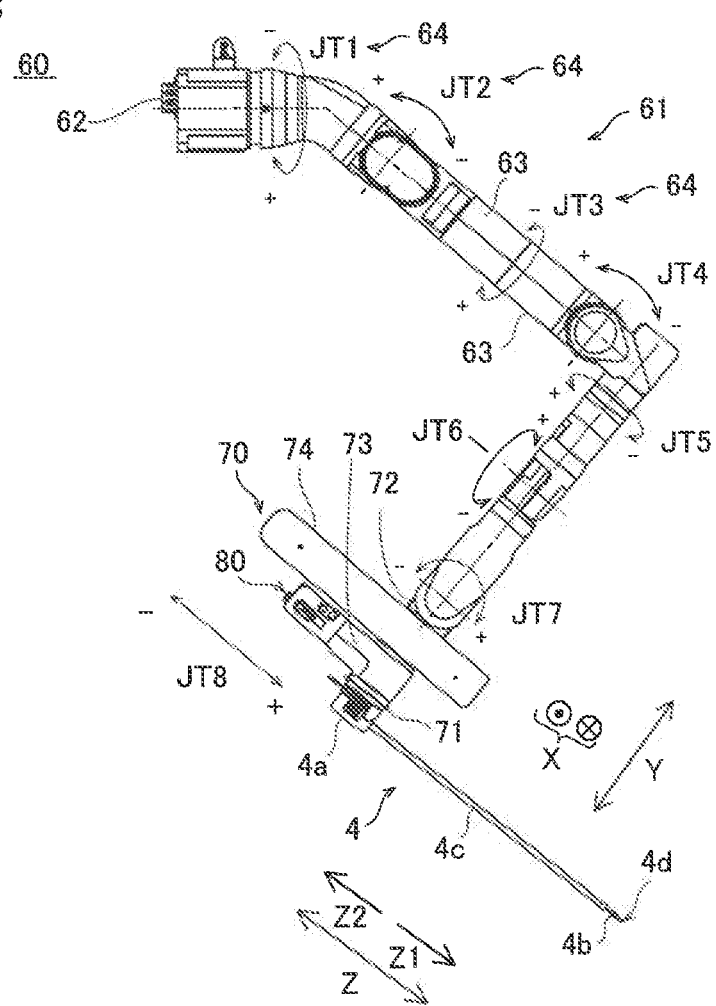
FIG. 8 is a diagram showing the configuration of a manipulator arm of the medical manipulator according to the embodiment of the present disclosure.

As shown in FIG. 8, each of the manipulator arms 60 includes an arm portion 61 and a translation mechanism 70 provided at the tip end of the arm portion 61. The arm portion 61 includes a base 62, links 63, and joints 64. The manipulator arms 60 three-dimensionally move the tip end sides with respect to the arm base 50 on the base sides of the manipulator arms 60. The arm portion 61 includes a 7-axis articulated robot arm. The plurality of manipulator arms 60 have the same configuration as each other.

Figure 13:
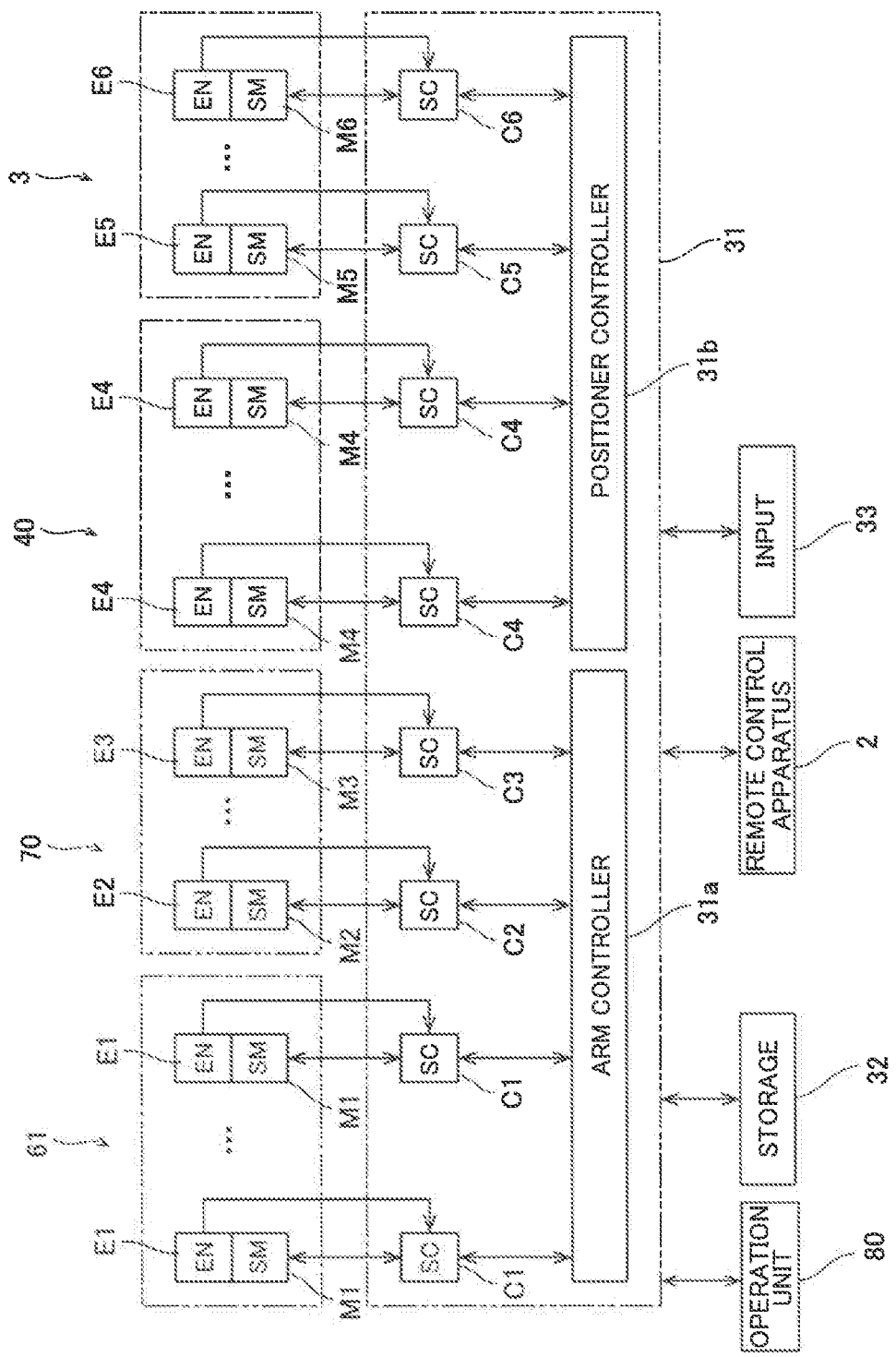
FIG. 13 is a block diagram showing the configuration of a controller of the medical manipulator according to the embodiment of the present disclosure.

Each of the manipulator arms 60 includes JT1 to JT7 axes as rotation axes and a JT8 axis as a linear motion axis. The JT1 to JT7 axes correspond to the rotation axes of the joints 64 of the arm portion 61. Furthermore, the JT7 axis corresponds to a base end side link 72 of the translation mechanism 70. The JT8 axis corresponds to an axis along which a tip end side link 73 of the translation mechanism 70 is moved relative to the base end side link 72 along the Z direction. That is, servomotors M1 shown in FIG. 13 are provided on the JT1 to JT7 axes of the manipulator arm 60, respectively. Furthermore, a servomotor M3 is provided on the JT8 axis.

The translation mechanism 70 is arranged on the tip end side of the arm portion 61, and the surgical instrument 4 is attached thereto. The translation mechanism 70 translates the surgical instrument 4 in a direction in which the surgical instrument 4 is inserted into the patient P. Furthermore, the translation mechanism 70 translates the surgical instrument 4 relative to the arm portion 61. Specifically, the translation mechanism 70 includes the holder 71 that holds the surgical instrument 4. The servomotors M2 shown in FIG. 13 are housed in the holder 71.

Figure 9:
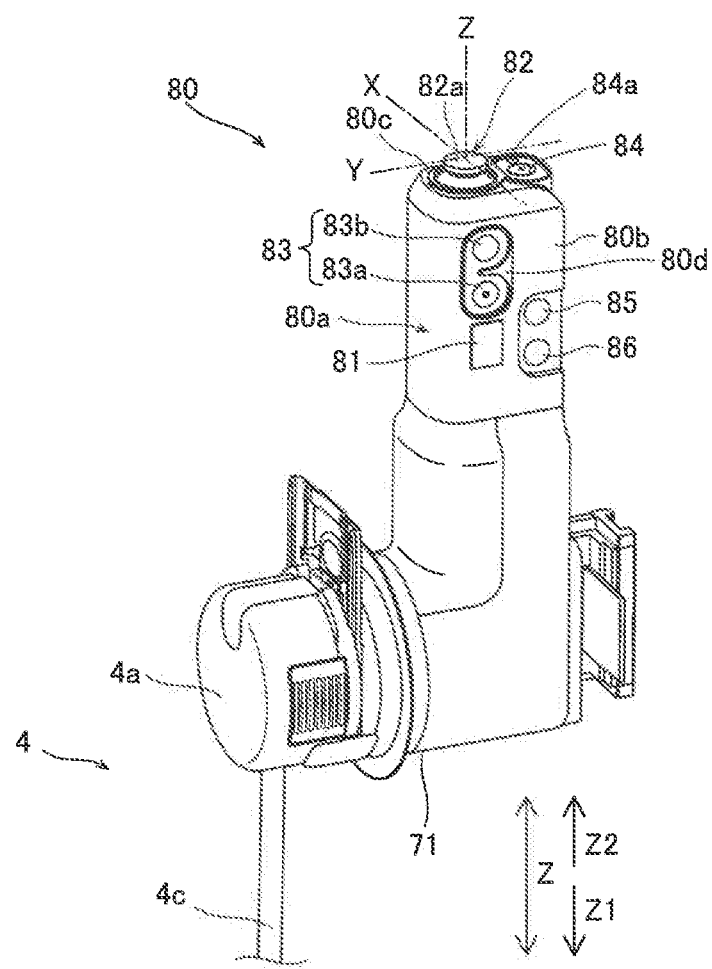
FIG. 9 is a perspective view showing the configuration of an operation unit of the medical manipulator according to the embodiment of the present disclosure.

As shown in FIG. 8, the medical manipulator 1 includes an operation unit 80 attached to each of the manipulator arms 60 to operate the manipulator arm 60. As shown in FIG. 9, the operation unit 80 includes an enable switch 81, a joystick 82, and a switch unit 83. The enable switch 81 allows or disallows movement of the manipulator arm 60 through the joystick 82 and the switch unit 83. The enable switch 81 gets into a state of allowing movement of the surgical instrument 4 by the manipulator arm 60 when the operator such as a nurse or an assistant grasps the operation unit 80 and presses the enable switch 81.

The switch unit 83 includes a switch 83a to move the surgical instrument 4 in the direction in which the surgical instrument 4 is inserted into the patient P, along the longitudinal direction of the surgical instrument 4, and a switch 83b to move the surgical instrument 4 in a direction opposite to the direction in which the surgical instrument 4 is inserted into the patient P. Both the switch 83a and the switch 83b are push-button switches.

Figure 10:
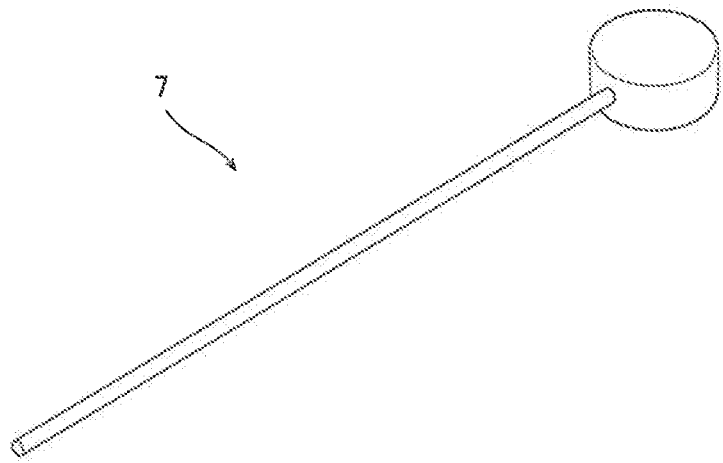
FIG. 10 is a diagram showing a pivot position teaching instrument.
Figure 12:
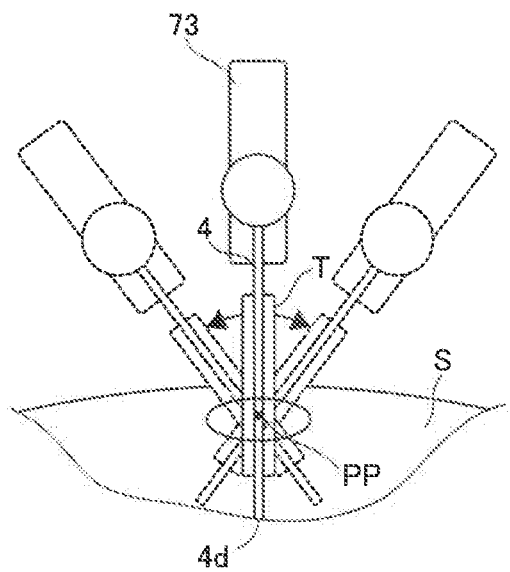
FIG. 12 is a diagram for illustrating rotation of the manipulator arm.

As shown in FIG. 9, the operation unit 80 includes a pivot button 85 to set a pivot position PP that serves as a fulcrum shown in FIG. 12 for movement of the surgical instrument 4 attached to the manipulator arm 60. The pivot button 85 is arranged adjacent to the enable switch 81 on a surface 80b of the operation unit 80. The pivot button 85 is pressed while the tip end of the endoscope 6 shown in FIG. 7 or a pivot position teaching instrument 7 shown in FIG. 10 is moved to a position corresponding to the insertion position of a trocar T inserted into the body surface S of the patient P such that the pivot position PP is set and stored in the storage 32. In the setting of the pivot position PP, the pivot position PP is set as one point, and the direction of the surgical instrument 4 is not set.

As shown in FIG. 1, the endoscope 6 is attached to one of the plurality of manipulator arms 60, which is a manipulator arm 60c, for example, and surgical instruments 4 other than the endoscope 6 are attached to remaining manipulator arms 60a, 60b, and 60d, for example. Specifically, in surgery, the endoscope 6 is attached to one of four manipulator arms 60, and the surgical instruments 4 other than the endoscope 6, such as pairs of forceps, are attached to the three manipulator arms 60. The pivot position PP is set with the endoscope 6 attached to the manipulator arm 60 to which the endoscope 6 is to be attached. Furthermore, pivot positions PP are set with pivot position teaching instruments 7 attached to the manipulator arms 60 to which the surgical instruments 4 other than the endoscope 6 are to be attached. The endoscope 6 is attached to one of two manipulator arms 60b and 60c arranged in the center among the four manipulator arms 60 arranged adjacent to each other. That is, the pivot position PP is individually set for each of the plurality of manipulator arms 60.

As shown in FIG. 9, an adjustment button 86 for optimizing the position of the manipulator arm 60 is provided on the surface 80b of the operation unit 80. After the pivot position PP for the manipulator arm 60 to which the endoscope 6 has been attached is set, the adjustment button 86 is pressed such that the positions of the other manipulator arms 60 and the arm base 50 are optimized.

Figure 11:
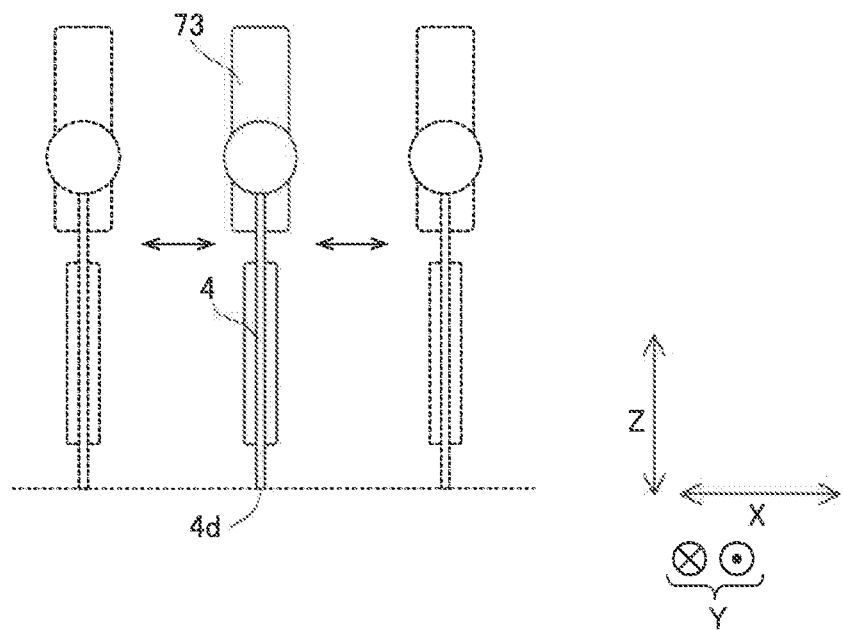
FIG. 11 is a diagram for illustrating translation of the manipulator arm.

As shown in FIG. 9, the operation unit 80 includes a mode switching button 84 to switch between a mode for translating the surgical instrument 4 attached to the manipulator arm 60, which is shown in FIG. 11, and a mode for rotationally moving the surgical instrument 4, which is shown in FIG. 12. Furthermore, a mode indicator 84a is provided in the vicinity of the mode switching button 84. The mode indicator 84a indicates a switched mode. Specifically, the mode indicator 84a is turned on to indicate a rotational movement mode and is turned off to indicate a translation mode.

The mode indicator 84a also serves as a pivot position indicator that indicates that the pivot position PP has been set.

As shown in FIG. 11, in the mode for translating the manipulator arm 60, the manipulator arm 60 is moved such that the tip end 4d of the surgical instrument 4 moves on an X-Y plane. As shown in FIG. 12, in the mode for rotationally moving the manipulator arm 60, when the pivot position PP is not set, the manipulator arm 60 is rotationally moved about the pair of forceps, and when the pivot position PP is set, the manipulator arm 60 is moved such that the surgical instrument 4 is rotationally moved about the pivot position PP as a fulcrum. The surgical instrument 4 is rotationally moved while the shaft 4c of the surgical instrument 4 is inserted into the trocar T.

As shown in FIG. 13, the manipulator arm 60 includes a plurality of servomotors M1, encoders E1, and speed reducers so as to correspond to a plurality of joints 64 of the arm portion 61. The encoders E1 detect the rotation angles of the servomotors M1. The speed reducers slow down rotation of the servomotors M1 to increase the torques.

The translation mechanism 70 includes a plurality of servomotors M2 to rotate rotary bodies provided in the driven unit 4a of the surgical instrument 4, the servomotor M3 to translate the surgical instrument 4, a plurality of encoders E2, an encoder E3, and a plurality of speed reducers. The encoders E2 and E3 detect the rotation angles of the servomotors M2 and M3, respectively. The plurality of speed reducers slow down rotation of the servomotors M2 and M3 to increase the torques.

The positioner 40 includes a plurality of servomotors M4, encoders E4, and speed reducers so as to correspond to a plurality of joints 43 of the positioner 40. The encoders E4 detect the rotation angles of the servomotors M4. The speed reducers slow down rotation of the servomotors M4 to increase the torques.

Figure 16:
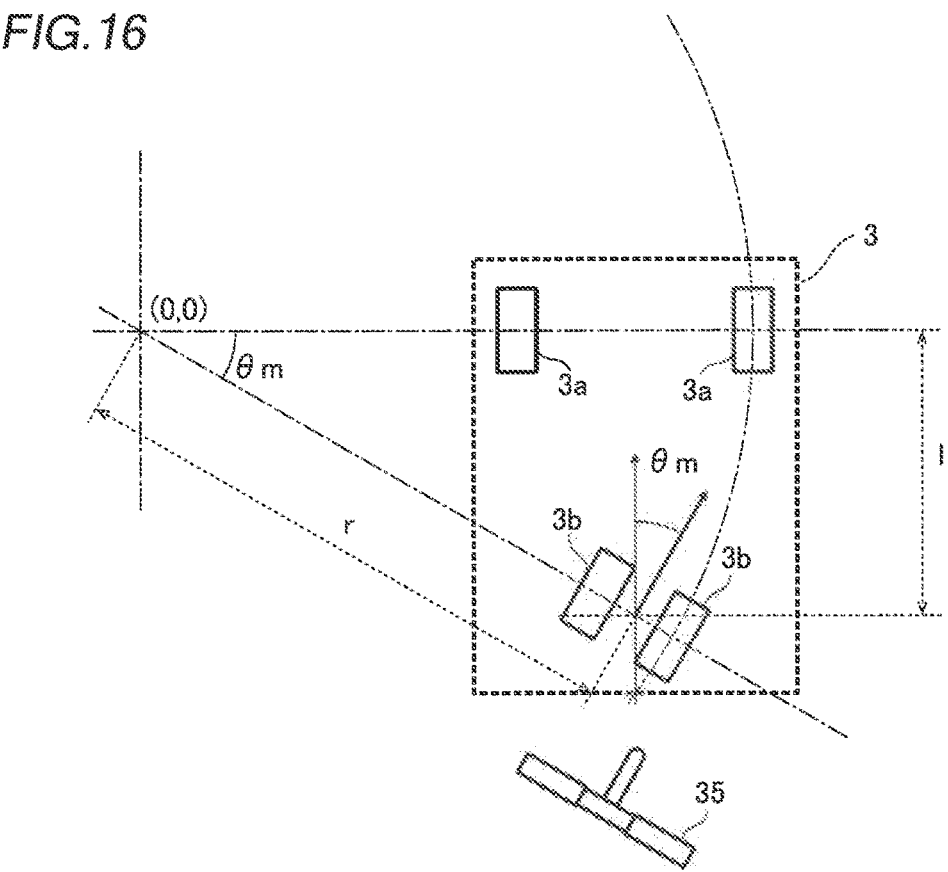
FIG. 16 is a diagram for illustrating calculation of the turning radius of the medical cart.

In this embodiment, as shown in FIG. 16, the medical cart 3 includes front wheels 3a as drive wheels and rear wheels 3b steered by the operation handle 35. The rear wheels 3b are arranged closer to the operation handle 35 than the front wheels 3a. As shown in FIG. 13, the medical cart 3 includes a servomotor M5 to drive each of a plurality of front wheels 3a of the medical cart 3, an encoder E5, a speed reducer, and a brake. The speed reducer slows down rotation of the servomotor M5 to increase the torque. Furthermore, a potentiometer P1 shown in FIG. 3 is provided on the operation handle 35 of the medical cart 3, and the servomotors M5 of the front wheels 3a are driven based on a rotation angle detected by the potentiometer P1 according to the twist of the throttle 35a. The rear wheels 3b of the medical cart 3 are of the dual wheel type, and the rear wheels are steered based on the rightward-leftward operation of the operation handle 35. Furthermore, a potentiometer P2 shown in FIG. 2 is provided on the operation handle 35 of the medical cart 3, and servomotors M6, encoders E6, and speed reducers are provided on the rear wheels 3b of the medical cart 3. The speed reducers slow down rotation of the servomotors M6 to increase the torques. The servomotors M6 are driven based on a rotation angle detected by the potentiometer P2 according to the rightward-leftward operation of the operation handle 35. That is, steering of the rear wheels 3b by the rightward-leftward operation of the operation handle 35 is power-assisted by the servomotors M6.

The medical cart 3 moves in the forward-rearward direction by driving the front wheels 3a. Furthermore, the operation handle 35 of the medical cart 3 is rotated such that the rear wheels 3b are steered, and the medical cart 3 moves in a rightward-leftward direction.

The controller 31 of the medical cart 3 includes an arm controller 31a to control movement of the plurality of manipulator arms 60 based on commands, and a positioner controller 31b to control movement of the positioner 40 and driving of the front wheels 3a of the medical cart 3 based on commands. Servo controllers C1 that control the servomotors M1 to drive the manipulator arm 60 are electrically connected to the arm controller 31a. The encoders E1 that detect the rotation angles of the servomotors M1 are electrically connected to the servo controllers C1.

Servo controllers C2 that controls the servomotors M2 to drive the surgical instrument 4 are electrically connected to the arm controller 31a. The encoders E2 that detect the rotation angles of the servomotors M2 are electrically connected to the servo controllers C2. A servo controller C3 that controls the servomotor M3 to translate the translation mechanism 70 is electrically connected to the arm controller 31a. The encoder E3 that detects the rotation angle of the servomotor M3 is electrically connected to the servo controller C3.

An operation command input to the remote control apparatus 2 is input to the arm controller 31a. The arm controller 31a generates a position command based on the input operation command and the rotation angle detected by the encoder E1, E2, or E3, and outputs the position command to the servo controller C1, C2, or C3. The servo controller C1, C2, or C3 generates a current command based on the position command input from the arm controller 31a and the rotation angle detected by the encoder E1, E2, or E3, and outputs the current command to the servomotor M1, M2, or M3. Thus, the manipulator arm 60 is moved according to the operation command input to the remote control apparatus 2.

The arm controller 31a of the controller 31 operates the manipulator arm 60 based on an input signal from the joystick 82 of the operation unit 80. Specifically, the arm controller 31a generates position commands based on the input signal (operation command) input from the joystick 82 and the rotation angles detected by the encoders E1, and outputs the position commands to the servo controllers C1. The servo controllers C1 generate current commands based on the position commands input from the arm controller 31a and the rotation angles detected by the encoders E1, and output the current commands to the servomotors M1. Thus, the manipulator arm 60 is moved according to the operation command input to the joystick 82.

The arm controller 31a of the controller 31 operates the manipulator arm 60 based on an input signal from the switch unit 83 of the operation unit 80. Specifically, the arm controller 31a generates a position command based on the input signal (operation command) input from the switch unit 83 and the rotation angle detected by the encoders E1 or the encoder E3, and outputs the position command to the servo controllers C1 or the servo controller C3. The servo controllers C1 or the servo controller C3 generates a current command based on the position command input from the arm controller 31a and the rotation angle detected by the encoders E1 or the encoder E3, and outputs the current command to the servomotors M1 or the servomotor M3. Thus, the manipulator arm 60 is moved according to the operation command input to the switch unit 83.

Servo controllers C4 that control the servomotors M4 to move the positioner 40 are electrically connected to the positioner controller 31b. The encoders E4 that detect the rotation angles of the servomotors M4 are electrically connected to the servo controllers C4. Servo controllers C5 that control the servomotors M5 to drive the front wheels 3a of the medical cart 3 are electrically connected to the positioner controller 31b. The encoders E5 that detect the rotation angles of the servomotors M5 are electrically connected to the servo controllers C5. Servo controllers C6 that control the servomotors M6 to drive the rear wheels 3b of the medical cart 3 are electrically connected to the positioner controller 31b. The encoders E6 that detect the rotation angles of the servomotors M6 are electrically connected to the servo controllers C6.

An operation command related to setting of a preparation position, for example, is input from the input 33 to the positioner controller 31b. The positioner controller 31b generates position commands based on the operation command input from the input 33 and the rotation angles detected by the encoders E4, and outputs the position commands to the servo controllers C4. The servo controllers C4 generate current commands based on the position commands input from the positioner controller 31b and the rotation angles detected by the encoders E4, and output the current commands to the servomotors M4. Thus, the positioner 40 is moved according to the operation command input to the input 33. Similarly, the positioner controller 31b moves the medical cart 3 based on an operation command from the input 33.

As described above, in this embodiment, as shown in FIG. 16, the medical cart 3 includes the front wheels 3a as drive wheels and the rear wheels 3b steered by the operation handle 35. Two front wheels 3a are arranged. The two front wheels 3a are arranged on the sides of the medical cart 3, respectively. Thus, when the rear wheels 3b are steered by the operation handle 35, the steered direction of the operation handle 35 and the turning direction of the medical cart 3 are opposite to each other. For example, when the operator rotates the operation handle 35 to the right, the medical cart 3 turns to the left. Therefore, it is difficult for the operator to intuitively understand the moving direction of the medical cart 3.

Figure 14:
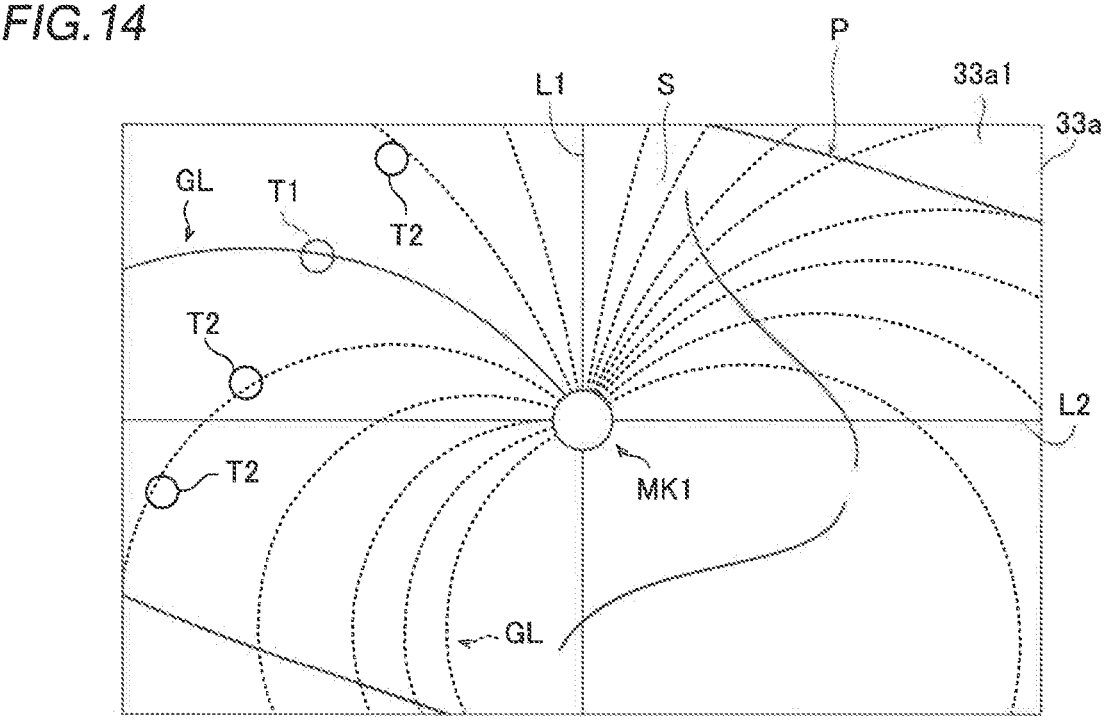
FIG. 14 is a block diagram showing the trocars, the marks, and a guideline displayed on the display.

Therefore, in this embodiment, as shown in FIG. 14, the image processing circuit 31c controls the display 33a to superimpose the guideline GL indicating the moving direction of the medical cart 3 based on the steering angle of the operation handle 35 on the image of the patient P captured by the imaging device 51 and display the guideline GL. Specifically, the image processing circuit 31c controls the display 33a to display the guideline GL based on the steering angle of the operation handle 35 and the position of the imaging device 51 with respect to the posture of the robot main body 1a. The posture of the robot main body 1a at the time of aligning the manipulator arms 60 with the surgical location in the patient P is called a roll-in posture. The guideline GL is an example of guide information.

In this embodiment, the guideline GL extends along the moving direction of the medical cart 3 with the vicinity of the center of a display screen 33a1 of the display 33a as the base end. The vicinity of the center of the display screen 33a1 indicates a concept including the center itself and the vicinity of the center. As described above, the display 33a displays an image of the first trocar T1 for inserting the endoscope 6 from the body surface S of the patient P, which is captured by the imaging device 51. Then, the image processing circuit 31c performs a control to display the first mark MK1 for aligning the robot main body 1a with the first trocar T1 at the center of the display screen 33a1 of the display 33a and display the guideline GL extending along the moving direction of the medical cart 3 with the first mark MK1 as the base end. Although the guideline GL extends from the outer peripheral edge of the first mark MK1 in FIG. 14, the guideline GL extending from the center of the first mark MK1 may be displayed. The first mark MK1 is an example of a mark.

In this embodiment, the guideline GL extends arcuately along the turning direction of the medical cart 3 that is turned by the operator steering the operation handle 35. That is, the guideline GL extends arcuately with the first mark MK1 as the base end. A method for calculating the guideline GL is described below.

In this embodiment, the image processing circuit 31c controls the display 33a to display the guideline GL when the medical cart 3 moves forward. The expression "when the medical cart 3 moves forward" refers to when the medical cart 3 moves so as to approach the patient P. That is, when the medical cart 3 moves rearward, the guideline GL is not displayed on the display 33a.

In this embodiment, the image processing circuit 31c controls the display 33a to update and display the guideline GL only while an enabling signal is received from the enable switch 35b. Specifically, the image processing circuit 31c calculates the guideline GL for each control cycle of the image processing circuit 31c, and controls the display 33a to update and display the calculated guideline GL only while the enable switch 35b is being pressed. That is, only one guideline GL is displayed on the display 33a. When the steering angle is changed by the operator steering the operation handle 35, the guideline GL corresponding to the changed steering angle is updated and displayed on the display 33a only while the enable switch 35b is being pressed. When the enable switch 35b is not pressed, the guideline GL before the update is displayed on the display 33a. For example, as shown in FIG. 14, the guideline GL corresponding to the current steering angle is shown by a solid line. When the steering angle is changed, the guideline GL shown by a dotted line in FIG. 14 is displayed so as to correspond to the changed steering angle.

Figure 15:
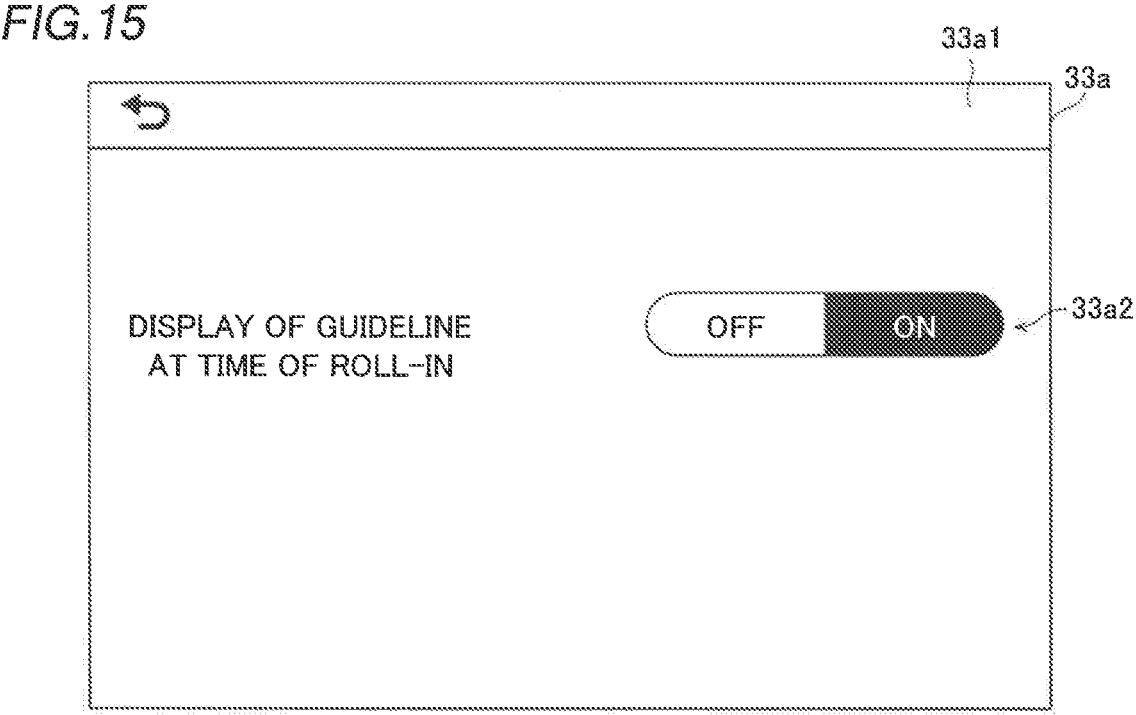
FIG. 15 is a diagram showing a selection operation unit for selecting to show or hide the guideline.

In this embodiment, as shown in FIG. 15, the medical manipulator 1 includes a selection operation unit 33a2 to allow the operator to select whether or not the guideline GL is displayed on the display 33a. Specifically, the selection operation unit 33a2 includes a touch button displayed on the display 33a. The selection operation unit 33a2 includes an ON button and an OFF button. When the operator presses the ON button, the guideline GL is displayed on the display 33a at the time of roll-in. When the operator presses the OFF button, the guideline GL is not displayed on the display 33a at the time of roll-in.

The method for the image processing circuit 31c to calculate the guideline GL is now described.

First, as shown in FIG. 16, the operation handle 35 of the medical cart 3 is steered by the operator. Thus, steering information of the operation handle 35 is input to the image processing circuit 31c. The image processing circuit 31c calculates the steering angle of the operation handle 35 based on the input steering information. Specifically, the steering angle is calculated by the following equation (1):

$$\theta m = (V_{tIN} - V_{FS}/2 - V_{to}) \times \varphi e/2 \qquad (1)$$

where θm represents the steering angle of the operation handle 35, $V_{IN}$ represents a voltage input to the potentiometer P2, $V_{FS}$ represents the full-scale voltage of the potentiometer P2, $V_{to}$ represents an offset adjustment voltage, and $\varphi_e$ represents the one-sided effective electric angle of the potentiometer P2.

Figure 17:
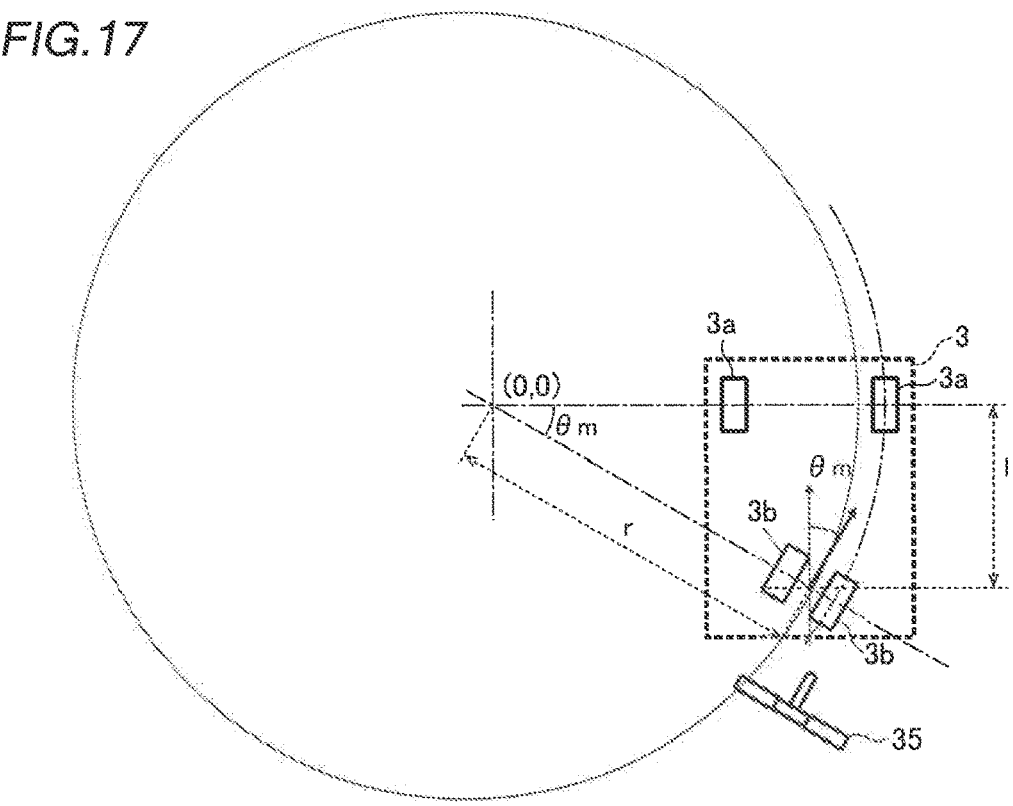
FIG. 17 is another diagram for illustrating the calculation of the turning radius of the medical cart.

As shown in FIG. 17, the image processing circuit 31c calculates the radius of a circle along which the medical cart 3 moves with the steering of the operation handle 35, based on the following equation (2):

$$r = l / \sin(\theta m) \qquad (2)$$

where r represents the radius of the circle along which the medical cart 3 moves, and l represents the wheelbase of the medical cart 3. The wheelbase refers to a distance between the front wheels 3a and the rear wheels 3b when the medical cart 3 is viewed from the side.

The image processing circuit 31c calculates the coordinates (X, Y) of each of the rear wheels 3b based on the following equations (3-1) to (3-3) with the center coordinates of the circle as (0, 0).

$$X = r \times \cos(\theta m) \qquad (3-1)$$

$$X = r \times \cos(\theta m) \times (-1) \qquad (3-2)$$

$$Y = l \times (-1) \qquad (3-3)$$

The equation (3-1) expresses an X coordinate in a case in which the medical cart 3 turns to the left, and the equation (3-2) expresses an X coordinate in a case in which the medical cart 3 turns to the right.

Figure 18:
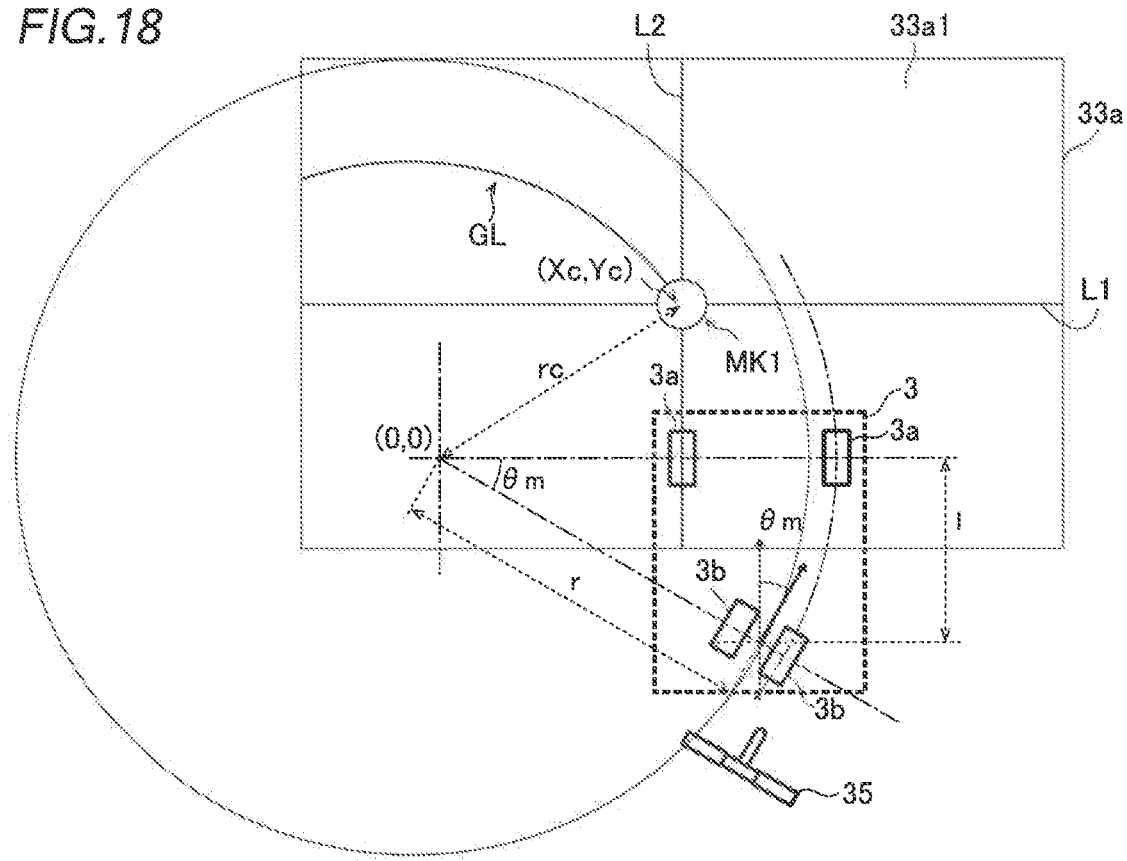
FIG. 18 is a diagram for illustrating calculation of the radii of the guideline displayed on the display.
Figure 19:
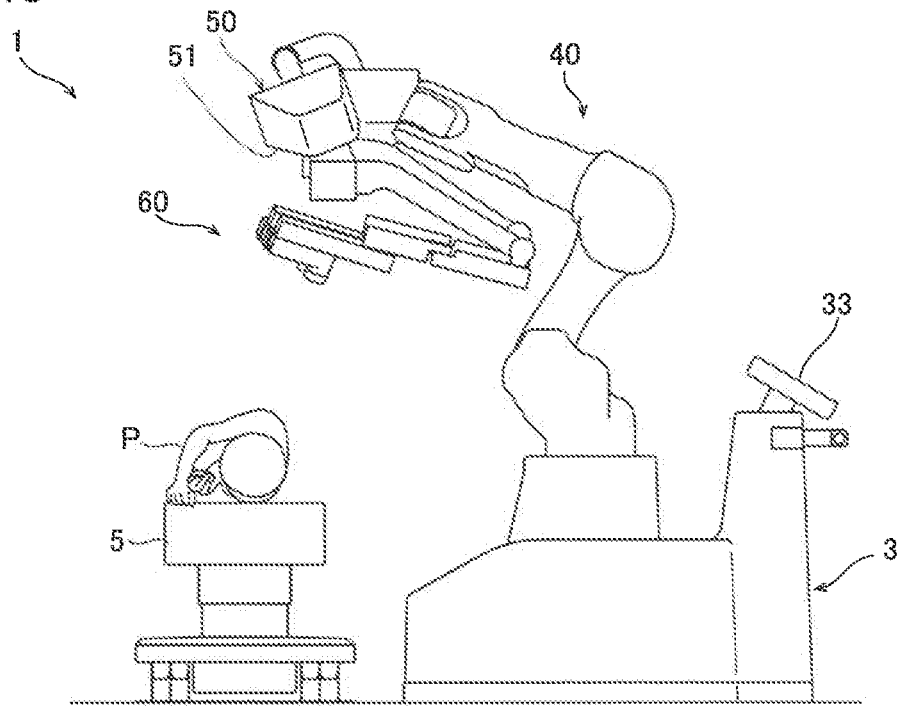
FIG. 19 is a diagram showing a roll-in posture different from FIG. 4.

Then, as shown in FIG. 18, the image processing circuit 31c calculates the center coordinates of the imaging device 51 and the radius rc of the arcuate guideline GL displayed on the display 33a. The position of the imaging device 51 on a horizontal plane differs depending on the roll-in posture. Examples of the roll-in posture include a posture in which the four manipulator arms 60 are arranged orthogonal to a direction from the head to the foot of the patient P, as shown in FIG. 4, and a posture in which the four manipulator arms 60 are arranged along the direction from the head to the foot of the patient P, as shown in FIG. 19. Thus, the position of the imaging device 51 on the horizontal plane differs depending on the roll-in posture. Even when the roll-in posture changes, the height of the imaging device 51 does not change.

Then, the image processing circuit 31c calculates the center coordinates (Xc, Yc) of the imaging device 51 with the center coordinates of the circle as (0, 0) and the radius rc of the arcuate guideline GL displayed on the display 33a based on the position of the imaging device 51 in each roll-in posture and the coordinates (X, Y) of each of the rear wheels 3b of the medical cart 3 from the following equations (4-1) to (4-3).

Specifically, in each roll-in posture, Xc, which is the X coordinate of the center position of the imaging device 51, is determined depending on a moving direction in which the medical manipulator 1 is rolled in and whether the medical cart 3 is turned to the left or to the right by the following equation (4-1).

$$Xc = X - 400 \text{ or } X + 400 \qquad (4-1)$$

In each roll-in posture, Yc, which is the Y coordinate of the center position of the imaging device 51, is determined depending on the roll-in posture by the following equation (4-2).

$$Yc = 760, 1340, \text{ or } 660 \qquad (4-2)$$

The radius rc of the arcuate guideline GL displayed on the display 33a is calculated by the following equation (4-3) using the Pythagorean theorem.

$$rc = \sqrt{(Xc^2 + Yc^2)} \qquad (4-3)$$

Then, as shown in FIG. 14, the image processing circuit 31c performs a control to superimpose the guideline GL on the image of the patient P captured by the imaging device 51 and display the guideline GL on the display screen 33a1 of the display 33a based on the calculated radius rc of the guideline GL. The operator steers the operation handle 35 such that the guideline GL is aligned with the first trocar T1.

Control Method of Medical Manipulator

A control method at the time of roll-in of the medical manipulator 1 is now described. One first trocar T1 and three second trocars T2 are inserted in advance into the body surface S of the patient P. The height of the arm base 50 is fixed. Furthermore, it is assumed that display of the guideline GL on the display 33a has been selected through the selection operation unit 33a2.

Figure 20:
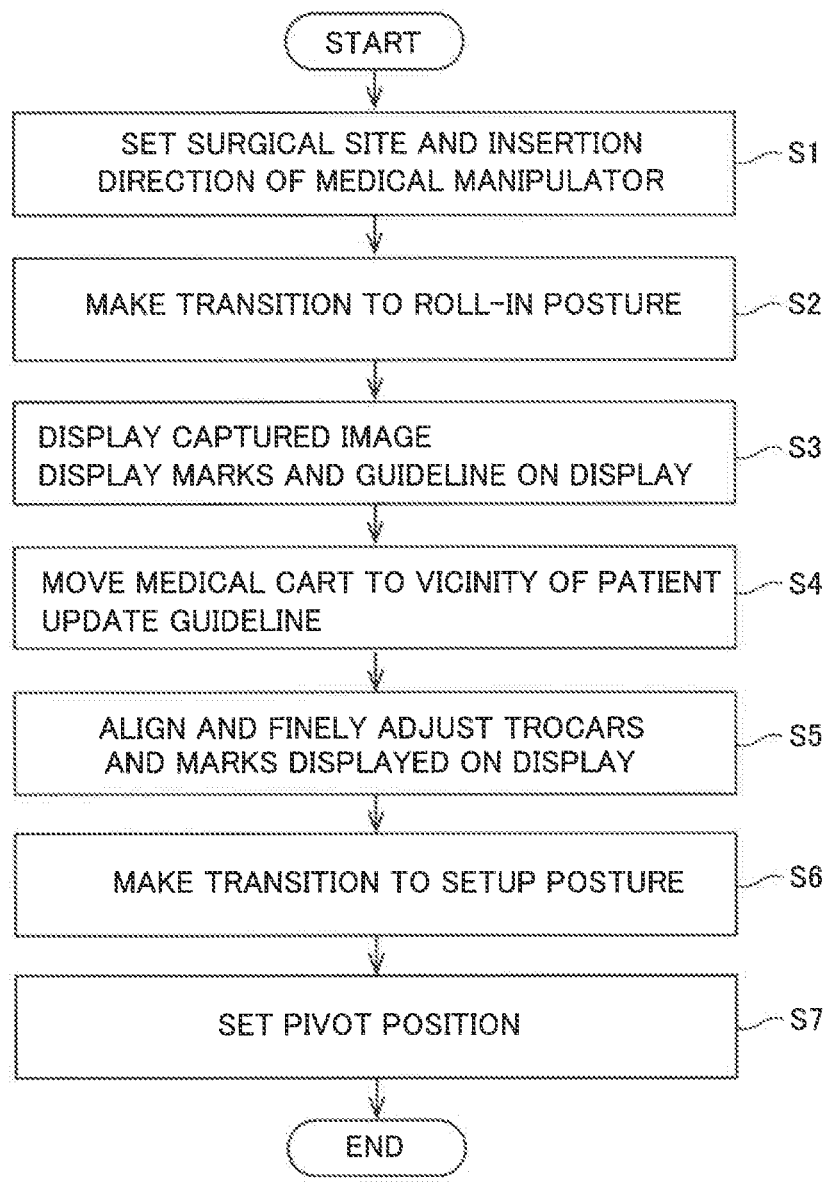
FIG. 20 is a flowchart for illustrating a control method of the medical manipulator according to the embodiment of the present disclosure.
Figure 21:
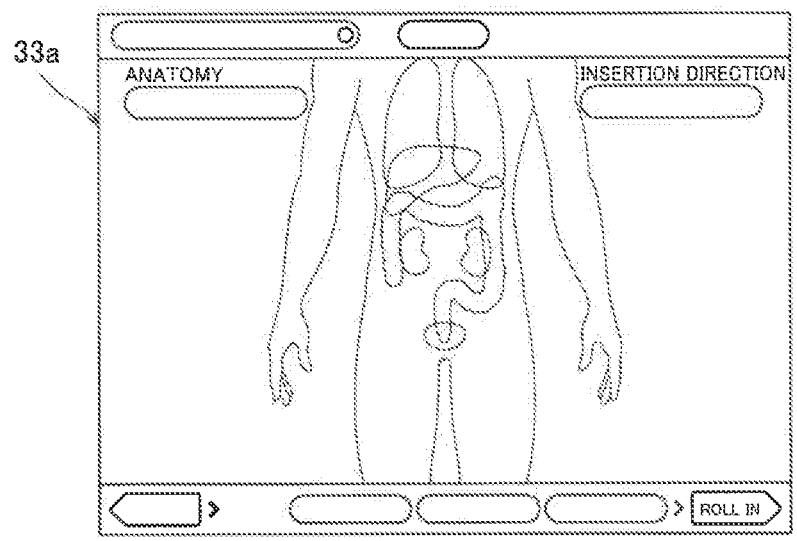
FIG. 21 is a diagram showing the display of the medical cart according to the embodiment of the present disclosure.
Figure 22:
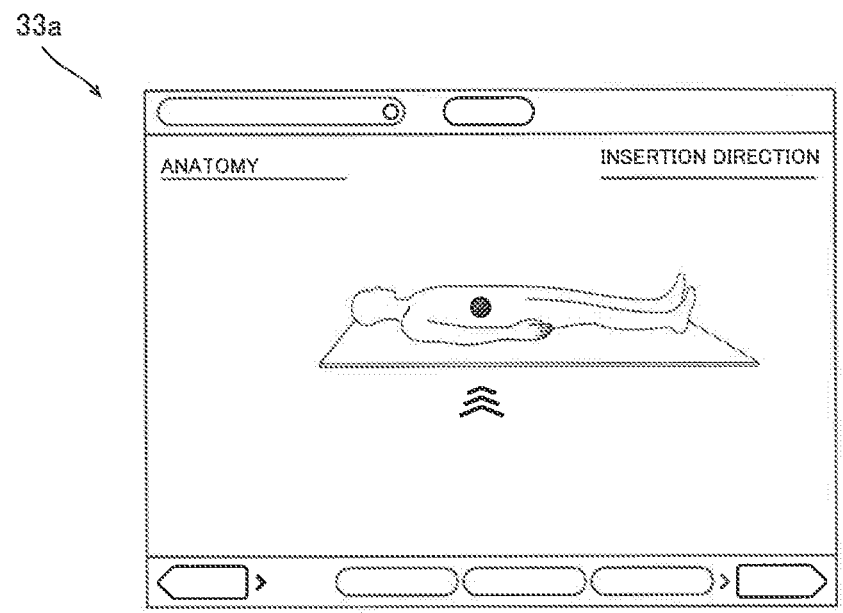
FIG. 22 is another diagram showing the display of the medical cart according to the embodiment of the present disclosure.

First, as shown in FIG. 20, in step S1, the roll-in of the medical manipulator 1 is prepared. Specifically, as shown in FIGS. 21 and 22, a surgical site and the insertion direction of the medical manipulator 1 with respect to the patient P are selected on the display 33a. The surgical site is an abdomen, for example. The insertion direction is from the right side, for example.

Then, in step S2, a roll-in button displayed on the display 33a is pressed. Thus, a roll-in mode is set, and the movement operation of the arm base 50 and the manipulator arm 60 is controlled such that the medical manipulator 1 takes the roll-in posture. The roll-in posture refers to a posture in which each manipulator arm 60 is folded so as not to interfere with the patient P when the manipulator arm 60 is positioned above the patient P by movement of the medical manipulator 1, the arm base 50 is arranged by the positioner 40 such that the imaging device 51 arranged on the arm base 50 can image a region vertically therebelow, and the arm base 50 is arranged by the positioner 40 such that the arrangement direction of each manipulator arm 60 corresponds to the surgical site and the insertion direction based on the information on the surgical site selected in step S1 and the information on the insertion direction selected in step S1. That is, after the roll-in button displayed on the display 33a is pressed such that a transition to the roll-in mode is made, when the joystick 33b is operated while the enable switch 33c is being pressed to allow the positioner 40 to move, the controller 31 moves the positioner 40 and each manipulator arm 60 such that the medical manipulator 1 automatically takes the roll-in posture.

Figure 23:
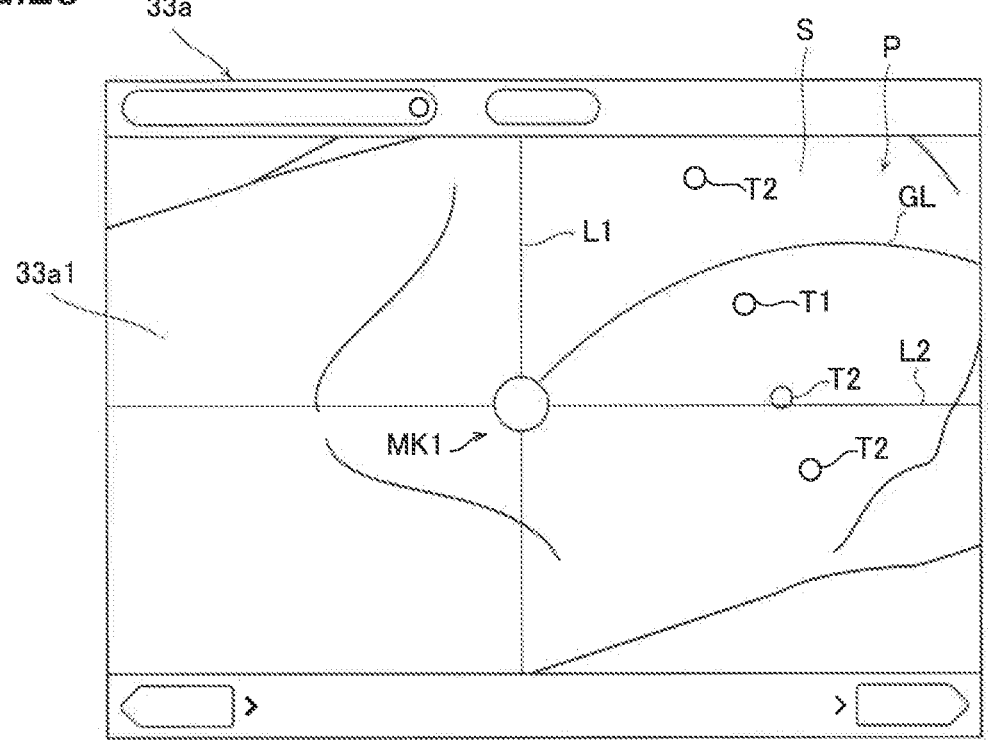
FIG. 23 is a diagram showing alignment between the trocars and the marks displayed on the display.

Then, in step S3, as shown in FIG. 23, after the movement operation of the manipulator arm 60, a screen of the display 33a is switched to an image captured by the imaging device 51. That is, the image captured by the imaging device 51 arranged on the arm base 50 is started to be displayed. Thus, the image of the patient P is displayed on the display 33a. Furthermore, the display 33a displays the marks MK including the first mark MK1 and the second mark MK2. In this imaging, a moving image is captured. The positioner 40 is controlled to move the arm base 50 such that the arrangement directions of the plurality of manipulator arms 60 correspond to the surgical site and the insertion direction of the medical manipulator 1 with respect to the patient P based on an input of the information on the surgical site, an input of the information on the insertion direction of the medical manipulator 1 with respect to the patient P, and an input of mode setting for aligning the arm base 50 with the patient P.

In the roll-in posture, when the arm base 50 is rotationally moved in the horizontal plane such that the arrangement direction of each manipulator arm 60 corresponds to the surgical site and the insertion direction selected in step S1, the captured image is corrected to be rotated in a direction opposite to the rotation of the arm base 50 and is displayed on the display 33a. Thus, the operator such as a nurse or a technician can start moving the medical manipulator 1 while looking at the image of the patient P, the orientation of which has been corrected to correspond to the orientation of the operator.

In this embodiment, the image processing circuit 31c receives a steering operation on the operation handle 35 of the medical cart 3. Then, the image processing circuit 31c controls the display 33a to superimpose the guideline GL indicating the moving direction of the medical cart 3 based on the steering angle of the operation handle 35 on the image of the patient P captured by the imaging device 51 and display the guideline GL.

When the operation handle 35 is not rotated to the right or left, the first line L1 of the second mark MK2 and the guideline GL displayed on the display 33a coincide with the moving direction of the medical cart 3. The first line L1 and the guideline GL are displayed semi-transparently, and thus they can be identified even when they are displayed in an overlapping manner. Furthermore, the first line L1 and the second line L2 displayed on the display 33a are fixed on the display 33a. The image displayed on the display 33a changes with movement of the arm base 50 or movement of the medical cart 3.

Then, in step S4, as shown in FIG. 23, the medical cart 3 is moved to the vicinity of the patient P placed on the surgical table 5, and the imaging device 51 arranged on the arm base 50 images the patient P placed on the surgical table 5 and having the trocars T inserted into the body surface S. Thus, the patient P having the trocars T inserted into the body surface S and imaged by the imaging device 51 is displayed on the display 33a. Furthermore, the marks MK aligned with the trocars T displayed on the display 33a are displayed on the display 33a. At this time, the relative positional relationship between the trocars T inserted into the body surface S of the patient P and the marks MK, which changes with movement of the arm base 50 due to movement of the medical cart 3, is displayed on the display 33a.

Specifically, on the display 33a, the substantially circular first mark MK1 and the cross-shaped second mark MK2 are displayed in advance. Then, on the display 33a, the body surface S of the patient P imaged by the imaging device 51 is displayed so as to overlap the first mark MK1 and the second mark MK2. Furthermore, the guideline GL is displayed on the display 33a so as to be superimposed on the image of the patient P.

The guideline GL is updated and displayed on the display 33a only while an enabling signal is received from the enable switch 35b. That is, the guideline GL is updated and displayed on the display 33a only while the enable switch 35b is being pressed and the medical cart 3 is moving.

Then, in step S5, the operator operates the operation handle 35 to move the medical cart 3 while visually recognizing the image captured by the imaging device 51 and displayed on the display 33a such that the first trocar T1 is arranged inside the substantially circular first mark MK1. In the roll-in posture, the arm base 50 is rotationally moved in the horizontal plane such that the arrangement direction of each manipulator arm 60 corresponds to the surgical site and the insertion direction selected in step S1, and thus on the display 33a, the plurality of second trocars T2 are arranged substantially on the first line L1 or the second line L2 of the second mark MK2 while the first trocar T1 is arranged inside the substantially circular first mark MK1.

In step S5, when the trocars T are misaligned with the first line L1 or the second line L2, the operator operates the joystick 33b while pressing the enable switch 33c such that the arm base 50 is rotationally moved in the horizontal plane. Thus, the position of the arm base 50 is finely adjusted. The image of the body surface S of the patient P is rotated with rotational movement of the medical cart 3 or the arm base 50. On the other hand, the first mark MK1 and the second mark MK2 are fixed on the display 33a. The magnification change button B is pressed to switch the magnification percentage of the image such that the operator can easily view the image.

Figure 24:
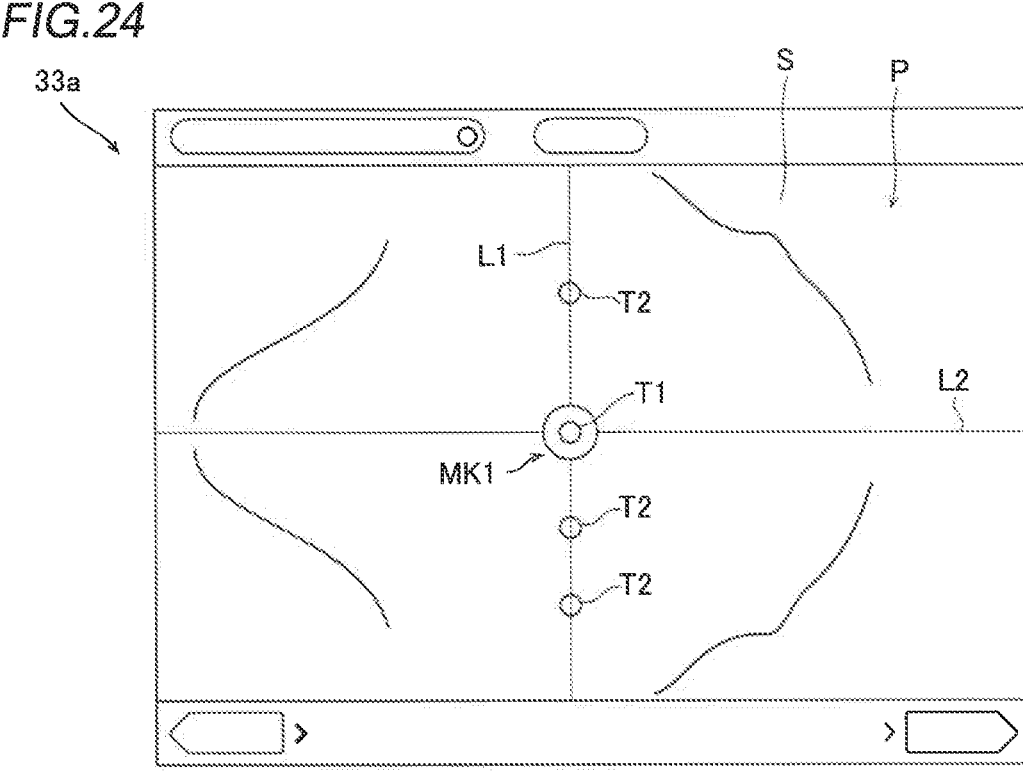
FIG. 24 is a diagram for illustrating the guideline displayed on the display.

Then, as shown in FIG. 24, the joystick 33b is operated such that the trocars T displayed on the display 33a and the marks MK are finely adjusted so as to be aligned with each other on the display 33a. Specifically, the position of the arm base 50 is finely adjusted by rotationally moving the arm base 50 in the horizontal plane such that the plurality of second trocars T2 are arranged on the first line L1 or the second line L2 of the second mark MK2 while the first trocar T1 is arranged inside the substantially circular first mark MK1. In FIG. 24, the arm base 50 is rotationally moved such that the plurality of second trocars T2 are arranged on the first line L1. Thus, roll-in of the medical manipulator 1 is completed. Depending on surgical technique, the plurality of second trocars T2 do not necessarily need to be arranged on the first line L1 or the second line L2 of the second mark MK2.

Then, in step S6, the plurality of manipulator arms 60 transition to a setup posture. The setup posture refers to a posture in which the plurality of manipulator arms 60 are further opened than in the roll-in posture so as to facilitate setting of the pivot position PP described below. After an arm preparation button on the display 33a is pressed such that a transition to a setup posture mode is made, the joystick 33b is operated while the enable switch 33c is being pressed to allow the positioner 40 to move such that the controller 31 moves the positioner 40 and the manipulator arms 60 to cause the medical manipulator 1 to take the setup posture. After a transition to the setup posture is made, a stabilizer mounted on the medical cart 3 is activated when a button for allowing the stabilizer displayed on the touch panel is pressed.

Then, in step S7, the endoscope 6 is attached to the manipulator arm 60 corresponding to the first trocar T1, and the pivot position PP is set. After the setting of the pivot position PP of the endoscope 6 is completed, the surgical instruments 4 other than the endoscope 6 are attached, and the pivot positions PP are set.

In step S5, the medical cart 3 is moved such that the first trocar T1 is arranged inside the first mark MK1, but the medical cart 3 may be moved to a position at which the patient P is arranged below the arm base 50 without aligning the first mark MK1 with the first trocar T1. In this case, in step S5, the operator operates the joystick 33b while pressing the enable switch 33c such that the arm base 50 is rotationally moved and translated in the horizontal plane so as to align the first mark MK1 with the first trocar T1 while the medical manipulator 1 maintains the roll-in posture.

Advantages of this Embodiment

According to this embodiment, the following advantages are achieved.

According to this embodiment, as described above, the image processing circuit 31c is configured or programmed to control the display 33a to superimpose the guideline GL indicating the moving direction of the medical cart 3 based on the steering angle of the operation handle 35 on the image of the patient P captured by the imaging device 51 and display the guideline GL. Accordingly, the image captured by the imaging device 51 is displayed on the display 33a together with the guideline GL, and thus the operator easily understands the relative positional relationship between the moving direction of the medical cart 3 and the patient P. Therefore, the operator can move the medical cart 3 to an appropriate position with respect to the patient P according to the guideline GL. Consequently, the manipulator arms 60 can be accurately positioned with respect to the patient P.

According to this embodiment, as described above, the image processing circuit 31c is configured or programmed to control the display 33a to display the guideline GL based on the steering angle of the operation handle 35 and the position of the imaging device 51 with respect to the posture of the robot main body 1a. Accordingly, the guideline GL can be displayed at an appropriate position on the display screen 33a1 of the display 33a based on the steering angle of the operation handle 35 and the position of the imaging device 51.

According to this embodiment, as described above, the guideline GL extends along the moving direction of the medical cart 3 with the vicinity of the center of the display screen 33a1 of the display 33a as the base end. Accordingly, the image captured by the imaging device 51 is displayed on the display 33a such that the center of the display screen 33a1 of the display 33a corresponds to the current position of the imaging device 51, and thus the operator can intuitively recognize the moving direction of the medical cart 3 from the current position by the guideline GL.

According to this embodiment, as described above, the medical cart 3 is turned by the operator steering the operation handle 35, and the guideline GL extends arcuately along the turning direction of the medical cart 3. Accordingly, the moving direction of the turning medical cart 3 can be appropriately displayed by the arcuate guideline GL.

According to this embodiment, as described above, the image processing circuit 31c is configured or programmed to perform a control to display the first mark MK1 for aligning the robot main body 1a with the first trocar T1 at the center of the display screen 33a1 of the display 33a and display the guideline GL extending along the moving direction of the medical cart 3 with the first mark MK1 as the base end. Accordingly, when the medical cart 3 is steered so as to align the first mark MK1 displayed at the center of the display screen 33a1 with the first trocar T1, the medical cart 3 can be appropriately steered along the guideline GL.

According to this embodiment, as described above, the image processing circuit 31c is configured or programmed to control the display 33a to display the guideline GL when the medical cart 3 moves forward. Accordingly, when the manipulator arms 60 are aligned with the surgical location in the patient P, the operator moves the medical cart 3 forward, and thus the operator can appropriately steer the medical cart 3 according to the guideline GL when the manipulator arms 60 are aligned with the surgical location in the patient P.

According to this embodiment, as described above, the image processing circuit 31c is configured or programmed to control the display 33a to update and display the guideline GL only while an enabling signal is received from the enable switch 35b. Accordingly, even when the steering angle of the operation handle 35 is changed while the enable switch 35b is being pressed to move the medical cart 3, the appropriate guideline GL can be displayed on the display 33a.

According to this embodiment, as described above, the medical manipulator 1 includes the selection operation unit 33a2 to allow the operator to select whether or not the guideline GL is displayed on the display 33a. Accordingly, the operator can select to show or hide the guideline GL as needed.

According to this embodiment, as described above, the selection operation unit 33a2 includes the touch button displayed on the display 33a. Accordingly, the touch button is displayed on the display 33a on which the image of the patient P and the guideline GL are displayed, and thus the convenience of the operator's operation can be improved as compared with a case in which the selection operation unit 33a2 is arranged in another portion.

According to this embodiment, as described above, the medical cart 3 includes the front wheels 3a as drive wheels and the rear wheels 3b steered by the operation handle 35. When the front wheels 3a are drive wheels and the rear wheels 3b are steering wheels, a direction in which the operation handle 35 is steered is opposite to a direction in which the medical cart 3 is turned. In this case, it is difficult for the operator to intuitively understand the moving direction of the medical cart 3 with respect to the steering. Therefore, it is particularly important to display the guideline GL indicating the moving direction of the medical cart 3 based on the steering angle of the operation handle 35 on the display 33a in terms of making it easier to intuitively understand the moving direction of the medical cart 3.

Modified Examples

The embodiment disclosed this time must be considered as illustrative in all points and not restrictive. The scope of the present disclosure is not shown by the above description of the embodiment but by the scope of claims for patent, and all modifications (modified examples) within the meaning and scope equivalent to the scope of claims for patent are further included.

For example, while the arcuate guideline GL is displayed on the display 33a in the aforementioned embodiment, the present disclosure is not limited to this. For example, an arrow indicating the moving direction of the medical cart 3 may alternatively be displayed on the display 33a.

While the position of the imaging device 51 is calculated based on the roll-in posture of the medical manipulator 1 in the aforementioned embodiment, the present disclosure is not limited to this. For example, the position of the imaging device 51 may alternatively be calculated based on a coordinate system for controlling the medical manipulator 1.

While the guideline GL is displayed with the first mark MK1 displayed at the center of the display screen 33a1 of the display 33a as the base end in the aforementioned embodiment, the present disclosure is not limited to this. For example, the guideline GL may alternatively be displayed with the center of the display screen 33a1 as the base end while the first mark MK1 is not displayed at the center of the display screen 33a1 of the display 33a.

While the guideline GL is displayed on the display 33a only when the medical cart 3 moves forward in the aforementioned embodiment, the present disclosure is not limited to this. For example, the guideline GL may alternatively be displayed on the display 33a both when the medical cart 3 moves forward and when it moves rearward.

While the display 33a is controlled to update and display the guideline GL only while an enabling signal is received from the enable switch 35b in the aforementioned embodiment, the present disclosure is not limited to this. For example, when the steering angle of the operation handle 35 is changed when the enabling signal is not received from the enable switch 35b, the guideline GL corresponding to the changed steering angle may be displayed.

While the height of the imaging device 51 does not change even when the roll-in posture changes in the aforementioned embodiment, the present disclosure is not limited to this. For example, the height of the imaging device 51 may alternatively change depending on the roll-in posture or during the roll-in. When the height of the imaging device 51 changes, the field of view of the imaging device 51 changes, and thus the positional relationship of the guideline GL with respect to the image of the patient P displayed on the display 33a becomes inappropriate. Therefore, the image processing circuit 31c acquires the height of the imaging device 51 based on a coordinate system for controlling the robot main body 1a. Then, the image processing circuit 31c controls the display 33a to display the guideline GL based on the steering angle of the operation handle 35, the planar position of the imaging device 51 with respect to the posture of the robot main body 1a, and the acquired height of the imaging device 51. Thus, the position of the guideline GL with respect to the image of the patient P displayed on the display 33a can be adjusted according to the acquired height of the imaging device 51, and thus even when the height of the imaging device 51 changes, the guideline GL can be displayed on the display 33a.

While the operator selects whether or not the guideline GL is displayed on the display 33a in the aforementioned embodiment, the present disclosure is not limited to this. For example, the guideline GL may always be displayed on the display 33a.

While the selection operation unit 33a2 includes the touch button displayed on the display 33a in the aforementioned embodiment, the present disclosure is not limited to this. For example, the selection operation unit 33a2 may alternatively include a push button switch or the like.

While the front wheels 3a of the medical cart 3 are drive wheels, and the rear wheels 3b are steering wheels in the aforementioned embodiment, the present disclosure is not limited to this. For example, the front wheels 3a of the medical cart 3 may alternatively be steering wheels, and the rear wheels 3b may alternatively be drive wheels.

While the four manipulator arms 60 are provided in the aforementioned embodiment, the present disclosure is not limited to this. In the present disclosure, the number of manipulator arms 60 may alternatively be any number as long as at least one manipulator arm 60 is provided.

While each of the arm portion 61 and the positioner 40 includes a 7-axis articulated robot in the aforementioned embodiment, the present disclosure is not limited to this. For example, each of the arm portion 61 and the positioner 40 may alternatively include an articulated robot having an axis configuration other than the 7-axis articulated robot. The axis configuration other than the 7-axis articulated robot refers to six axes or eight axes, for example.

While the medical manipulator 1 includes the medical cart 3, the positioner 40, and the arm base 50 in the aforementioned embodiment, the present disclosure is not limited to this. For example, the positioner 40 and the arm base 50 are not necessarily required, and the medical manipulator 1 may alternatively include only the medical cart 3 and the manipulator arms 60.

While the imaging device 51 is provided on the arm base 50 in the aforementioned embodiment, the present disclosure is not limited to this. For example, the imaging device 51 may alternatively be provided on the medical manipulator 1 or the positioner 40.

While the display 33a is provided on the medical cart 3 in the aforementioned embodiment, the present disclosure is not limited to this. For example, the display 33a may alternatively be provided on the positioner 40.

While the guideline GL is calculated in the image processing circuit 31c in the aforementioned embodiment, the present disclosure is not limited to this. For example, the guideline GL may alternatively be calculated in the controller 31.

The functionality of the elements disclosed herein may be implemented using circuitry or processing circuitry that includes general purpose processors, special purpose processors, integrated circuits, application specific integrated circuits (ASICs), conventional circuitry and/or combinations thereof that are configured or programmed to perform the disclosed functionality. Processors are considered processing circuitry or circuitry as they include transistors and other circuitry therein. In the present disclosure, the circuitry, units, or means are hardware that carries out or is programmed to perform the recited functionality. The hardware may be hardware disclosed herein or other known hardware that is programmed or configured to carry out the recited functionality. When the hardware is a processor that may be considered a type of circuitry, the circuitry, means, or units are a combination of hardware and software, and the software is used to configure the hardware and/or processor.

What is claimed is:

1. A surgical robot comprising:
   a robot main body including a manipulator arm to which a surgical instrument is attached;
   a medical cart including a steering device to receive a steering operation, the medical cart moving the robot main body based on the received steering operation;
   an imaging device on the robot main body;
   a display to display an image of a patient captured by the imaging device; and
   a controller configured or programmed to control the display to:
   display a mark at a fixed position on the display, the mark representing a relative position of the robot main body and the patient;
   superimpose guide information indicating a moving direction of the medical cart based on a steering angle of the steering device on the image captured by the imaging device and display the guide information; and
   change the guide information based on a change in the steering angle of the steering device.

2. The surgical robot according to claim 1, wherein the controller is configured or programmed to control the display to display the guide information based on the steering angle of the steering device and a position of the imaging device with respect to a posture of the robot main body.

3. The surgical robot according to claim 1, wherein the guide information includes a guideline extending along the moving direction of the medical cart from a vicinity of a center of a display screen of the display.

4. The surgical robot according to claim 3, wherein
   the medical cart is turned by steering the steering device; and
   the guideline extends arcuately along a turning direction of the medical cart.

5. The surgical robot according to claim 3, wherein
the display displays an image of a trocar for inserting an endoscope from a body surface of a patient, the image being captured by the imaging device; and
the controller is configured or programmed to perform a control to:
display the mark for aligning the robot main body with the trocar at the center of the display screen of the display; and
display the guideline extending along the moving direction of the medical cart based on the steering angle so as to enable the medical cart to be moved along the guideline to align the mark with the image of the trocar.

6. The surgical robot according to claim 1, wherein the controller is configured or programmed to control the display to display the guide information when the medical cart moves forward.

7. The surgical robot according to claim 1, wherein
the steering device further includes an enable switch to allow or disallow movement of the medical cart; and
the controller is configured or programmed to control the display to update and display the guide information only while an enabling signal is received from the enable switch.

8. The surgical robot according to claim 1, wherein the controller is configured or programmed to:
acquire a height of the imaging device based on a coordinate system for controlling the robot main body; and
control the display to display the guide information based on the steering angle of the steering device, a planar position of the imaging device with respect to a posture of the robot main body, and the acquired height of the imaging device.

9. The surgical robot according to claim 1, further comprising:
a selection operation unit to allow the operator to select whether or not the guide information is displayed on the display.

10. The surgical robot according to claim 9, wherein the selection operation unit includes a touch button displayed on the display.

11. The surgical robot according to claim 1, wherein 10 the medical cart includes a front wheel as a drive wheel and a rear wheel steered by the steering device.

12. A control method of a surgical robot, the control method comprising:
capturing an image by an imaging device;
displaying an image of a patient captured by the imaging device on a display;
receiving a steering operation on a steering device of a medical cart that moves a robot main body including a manipulator arm to which a surgical instrument is attached;
displaying a mark at a fixed position on the display, the mark representing a relative position of the robot main body and the patient;
superimposing guide information indicating a moving direction of the medical cart based on a steering angle of the steering device on the image captured by the imaging device and displaying the guide information on the display; and
changing the guide information based on changing the steering angle of the steering device.

13. The control method of a surgical robot according to claim 12, wherein the displaying of the guide information on the display includes displaying the guide information on the display based on the steering angle of the steering device and a position of the imaging device with respect to a posture of the robot main body.

14. The control method of a surgical robot according to claim 12, wherein the guide information includes a guideline extending along the moving direction of the medical cart from a vicinity of a center of a display screen of the display.

15. The control method of a surgical robot according to claim 14, wherein
the medical cart is turned by steering the steering device; and
the guideline extends arcuately along a turning direction of the medical cart.

16. The control method of a surgical robot according to claim 14, wherein
displaying the image of the patient captured by the imaging device on the display comprises displaying an image of a trocar for inserting an endoscope from a body surface of the patient, the image being captured by the imaging device; and
displaying the guide information on the display based on the steering angle of the steering device and the position of the imaging device with respect to the posture of the robot main body includes:
displaying the mark for aligning the robot main body with the trocar at the center of the display screen of the display; and
displaying the guideline extending along the moving direction of the medical cart based on the steering angle so as to enable the medical cart to be moved along the guideline to align the mark with the image of the trocar.

17. The control method of a surgical robot according to claim 12, wherein displaying of the guide information on the display includes displaying the guide information on the display when the medical cart moves forward.

18. The control method of a surgical robot according to claim 12, wherein
the steering device further includes an enable switch to allow or disallow movement of the medical cart; and
displaying the guide information on the display includes updating and displaying the guide information on the display only in response to receiving an enabling signal from the enable switch.

19. The control method of a surgical robot according to claim 12, wherein displaying the guide information on the display includes:
acquiring a height of the imaging device based on a coordinate system for controlling the robot main body; and
displaying the guide information on the display based on the steering angle of the steering device, a planar position of the imaging device with respect to a posture of the robot main body, and the acquired height of the imaging device.

20. The control method of a surgical robot according to claim 12, further comprising:
allowing an operator selection to select whether or not the guide information is displayed on the display.

* * * * *